(12) United States Patent
Hsiung et al.

(10) Patent No.: US 6,895,338 B2
(45) Date of Patent: May 17, 2005

(54) MEASURING AND ANALYZING MULTI-DIMENSIONAL SENSORY INFORMATION FOR IDENTIFICATION PURPOSES

(75) Inventors: Chang-Meng B. Hsiung, Irvine, CA (US); Jing Li, Temple City, CA (US); Beth Munoz, Pasadena, CA (US); Ajoy K. Roy, Pasadena, CA (US); Michael G. Steinthal, Los Angeles, CA (US); Steven A. Sunshine, Pasadena, CA (US); Michael A. Vicic, Pasadena, CA (US); Shou-Hua Zhang, Arcadia, CA (US)

(73) Assignee: Smiths Detection - Pasadena, Inc., Pasadena, CA (US)

( * ) Notice: Subject to any disclaimer, the term of this patent is extended or adjusted under 35 U.S.C. 154(b) by 44 days.

(21) Appl. No.: 09/802,513

(22) Filed: Mar. 9, 2001

(65) Prior Publication Data

US 2004/0215402 A1 Oct. 28, 2004

Related U.S. Application Data

(60) Provisional application No. 60/188,569, filed on Mar. 10, 2000, provisional application No. 60/188,588, filed on Mar. 10, 2000, and provisional application No. 60/188,589, filed on Mar. 10, 2000.

(51) Int. Cl.[7] .......................... G01N 31/00; G06F 19/00
(52) U.S. Cl. ...................... 702/22; 73/29.01; 422/82.01
(58) Field of Search .......................... 702/22; 73/29.01; 422/82.01

(56) References Cited

U.S. PATENT DOCUMENTS

| | | | |
|---|---|---|---|
| 5,410,492 A | 4/1995 | Gross et al. | |
| 5,459,675 A | 10/1995 | Gross et al. | |
| 5,571,401 A | 11/1996 | Lewis et al. | |
| 5,629,872 A | 5/1997 | Gross et al. | |
| 5,675,070 A | 10/1997 | Gelperin | |
| 5,697,326 A | 12/1997 | Mottram et al. | |
| 5,745,382 A | 4/1998 | Vilim et al. | |
| 5,761,090 A | 6/1998 | Gross et al. | |
| 5,764,509 A | 6/1998 | Gross et al. | |
| 5,774,379 A | 6/1998 | Gross et al. | |
| 5,788,833 A | 8/1998 | Lewis et al. | |
| 5,807,701 A | 9/1998 | Payne et al. | |
| 5,891,398 A | 4/1999 | Lewis et al. | |
| 5,926,804 A | 7/1999 | Tufts et al. | |
| 5,959,191 A | 9/1999 | Lewis et al. | |
| 5,987,399 A | 11/1999 | Wegerich et al. | |
| 6,196,057 B1 | 3/2001 | Discenzo | |
| 6,234,006 B1 | 5/2001 | Sunshine et al. | |
| 6,422,061 B1 * | 7/2002 | Sunshine et al. | 73/29.01 |
| 2001/0007985 A1 | 7/2001 | Rothberg et al. | |
| 2002/0141901 A1 * | 10/2002 | Lewis et al. | 422/82.01 |

FOREIGN PATENT DOCUMENTS

| | | |
|---|---|---|
| WO | WO 94/28557 | 12/1994 |
| WO | WO 97/08627 | 3/1997 |
| WO | WO 97/14105 | 4/1997 |
| WO | WO 97/49011 | 12/1997 |
| WO | WO 99/26073 | 5/1999 |
| WO | WO 99/36920 | 7/1999 |

* cited by examiner

Primary Examiner—John Barlow
Assistant Examiner—Aditya Bhat
(74) Attorney, Agent, or Firm—Foley & Lardner LLP

(57) ABSTRACT

Methods and systems are provides for measuring multi-dimensional sensing information for identification purposes. The identity of one or more substances is determined through analysis of multidimensional data that can include, among others, intrinsic information as well as extrinsic information. The method for identification of a substance comprises utilizing pattern recognition to form descriptors to identify characteristics of the substance. A system and computer program for performing analysis of the multidimensional data are also described.

56 Claims, 22 Drawing Sheets

MEASURING AND ANALYZING MULTI-DIMENSIONAL SENSORY INFORMATION FOR IDENTIFICATION PURPOSES

CROSS-REFERENCE TO RELATED APPLICATIONS

The present application claims priority to U.S. Provisional Patent Application Nos. 60/188,569, 60/188,588, and 60/188,589, all of which were filed on Mar. 10, 2000, the teachings of each application are hereby incorporated by reference for all purposes.

BACKGROUND OF THE INVENTION

This invention generally relates to techniques for identifying one or more substances using multidimensional data. More particularly, the present invention provides systems, methods, and computer code for classifying or identifying one or more substances using multi-dimensional data. The multidimensional data can include, among others, intrinsic information such as temperature, acidity, chemical composition, and color, as well as extrinsic information, such as origin, and age. Merely by way of example, the present invention is implemented using fluid substances, but it would be recognized that the invention has a much broader range of applicability. The invention can be applied to other settings such as chemicals, electronics, biological, medical, petrochemical, gaming, hotel, commerce, machining, electrical grids, and the like.

Techniques and devices for detecting a wide variety of analytes in fluids such as vapors, gases and liquids are well known. Such devices generally comprise an array of sensors that in the presence of an analyte produce a unique output signature. Using pattern recognition algorithms, the output signature, such as an electrical response, can be correlated and compared to the known output signature of a particular analyte or mixture of substances. By comparing the unknown signature with the stored or known signatures, the analyte can be detected, identified, and quantified. Examples of such detection devices can be found in U.S. Pat. No. 5,571,401 (Lewis et al.); U.S. Pat. No. 5,675,070 (Gelperin); U.S. Pat. No. 5,697,326 (Mottram et al.); U.S. Pat. No. 5,788,833 (Lewis et al.); U.S. Pat. No. 5,807,701 (Payne et al.); and U.S. Pat. No. 5,891,398 (Lewis et al.), the disclosures of which are incorporated herein by reference.

Generally all of these techniques rely upon a predetermined pattern recognition algorithm to analyze data to compare a known signature with an unknown signature to detect and identify an unknown analyte. These techniques, however, are often cumbersome. They also require highly manual data processing techniques. Additionally, each algorithm must often require manual input to be used with the known signature. Furthermore, there are many different types of algorithms, which must often be used. These different algorithms are often incompatible with each other and cannot be used in a seamless and cost effective manner. These and many other limitations are described throughout the present specification and more particularly below.

From the above, it is seen that an improved way to identify a characteristic of a fluid substance is highly desirable.

SUMMARY OF THE INVENTION

According to the present invention, a technique including systems, methods, and computer codes for identifying one or more substances using multidimensional data is provided. More particularly, the present invention provides systems, methods, and computer codes for classifying or identifying one or more substances using multi-dimensional data. The multidimensional data can include, among others, intrinsic information such as temperature, acidity, chemical composition, olfactory information, color, sugar content, as well as extrinsic information, such as origin, and age.

In one specific embodiment, the present invention provides a system including computer code for training computing devices for classification or identification purposes for one or more substances capable of producing olfactory information. The computer code is embedded in memory, which can be at a single location or multiple locations in a distributed manner. The system has a first code directed to acquiring at least first data from a first substance and second data from a second substance to a computing device. The data are comprised of a plurality of characteristics to identify the substance. The system also includes a second code directed to normalizing at least one of the characteristics for each of the first data and the second data. Next, the system includes computer code directed to correcting at least one of the characteristics for each of the first data and the second data. A code directed to processing one or more of the plurality of characteristics for each of the first data and the second data in the computing device using pattern recognition to form descriptors to identify the first substance or the second substance also is included. For purposes of this application, the term "descriptors" includes model coefficients/parameters, loadings, weightings, and labels, in addition to other types of information. A code directed to storing the set of descriptors into a memory device coupled to the computing device. The set of descriptions is for analysis purposes of one or a plurality of substances. This code and others can be used with the present invention to perform the functionality described herein as well as others.

In a further embodiment, the invention provides a computer program product or code in memory for preprocessing information for identification or classification purposes. Here, the code is stored in memory at a single location or distributed. The product includes a code directed to acquiring a voltage reading from a sensor of a sensing device. The sensor is one of a plurality of sensors that are disposed in an array. The code is also provided for determining if the voltage is outside a baseline voltage of a predetermined range. If the voltage is outside the predetermined range, the code is directed to reject the sensor of the sensing device for use in acquiring sensory information. In some embodiments, the present invention further comprises a code directed to exposing at least one of the sensors to a sample and acquiring a sample voltage from the sample, if the sample voltage is outside a predetermined sample voltage range, reject the one exposed sensor. This code and others can be used with the present invention to perform the functionality described herein as well as others.

In yet another embodiment, the present invention provides a system for classifying or identifying one or more substances capable of producing olfactory information. The system includes a process manager and an input module coupled to the process manager. The input module provides at least a first data from a first substance and second data from a second substance to a computing device. The data are comprised of a plurality of characteristics to identify the substance. The system also includes a normalizing module coupled to the process manager for normalizing at least one of the characteristics for each of the first data and the second data. A pattern recognition module is coupled to the process manager for processing one or more of the plurality of characteristics for each of the first data and the second data in the computing device using pattern recognition to form descriptors to identify the first substance or the second substance. An output module is coupled to the main process manager for storing the set of descriptors into a memory device coupled to the computing device. The set of descriptions is for analysis purposes of one or a plurality of substances. Depending upon the embodiment, other modules can also exist.

In still another specific embodiment, the present invention provides a method for training computing devices for classification or identification purposes for one or more substances capable of producing olfactory information. The method includes providing at least a first data from a first substance and second data from a second substance to a computing device. The data are comprised of a plurality of characteristics to identify the substance. The method also includes normalizing at least one of the characteristics for each of the first data and the second data. Next, the method includes correcting at least one of the characteristics for each of the first data and the second data. A step of processing one or more of the plurality of characteristics for each of the first data and the second data in the computing device using pattern recognition to form descriptors to identify the first substance or the second substance also is included. The method then stores the set of descriptors into a memory device coupled to the computing device. The set of descriptions is for analysis purposes of one or a plurality of substances.

In another alternative embodiment, the present invention provides a method for teaching a system used for analyzing multidimensional information for one or more substances, e.g., liquid, vapor, fluid. The method also includes providing a plurality of different substances. Each of the different substances is defined by a plurality of characteristics to identify any one of the substances from the other substances, the plurality of characteristics being provided in electronic form. The method also includes providing a plurality of processing methods. Each of the processing methods is capable of processing each of the plurality of characteristics to provide an electronic fingerprint for each of the substances. A step of processing each of the plurality of characteristics for each of the substances through a first processing method from the plurality of processing methods to determine relationships between each of the substances through the plurality of characteristics of each of the substances from the first processing method is also included. The method further includes processing each of the plurality of characteristics for each of the substances through a second processing method to determine relationships between each of the substances through the plurality of characteristics for each of the substances from the second processing method. The method includes processing each of the plurality of characteristics for each of the substances through an nth processing method to determine relationships between each of the substances through the plurality of characteristics from each of the substances from the nth processing method. The method compares the relationships from the first processing method to the relationships from the second processing method to the relationships from the nth processing method to find the processing method that yields the largest signal to noise ratio to identify each of the substances; and selects the processing method that yielded the largest signal to noise ratio. The relationships from the selected processing method provide an improved ability to distinguish between each of the substances using the selected processing method.

In still a further embodiment, the invention provides a method for preprocessing information for identification or classification purposes. The method includes acquiring a voltage reading from a sensor of a sensing device. The sensor is one of a plurality of sensors that are disposed in an array. The method also includes determining if the voltage is outside a baseline voltage of a predetermined range. If the voltage is outside of the predetermined range, the method rejects the sensor of the sensing device for use in acquiring sensory information. In some embodiments, the present invention further comprises exposing at least one of the sensors to a sample and acquiring a sample voltage from the sample, if the sample voltage is outside a predetermined sample voltage range, the method rejects the one exposed sensor.

In yet another embodiment, the present invention provides a system for identifying a substance capable of producing olfactory information. The system includes a user interface apparatus comprising a display, a graphical user interface, and a central processor. The system further includes a process manager operably coupled to the display through the central processor. The graphical user interface is capable of imputing an information object from a client to manipulate olfaction data and displaying the identity of a test substance received from a server.

Numerous benefits are achieved by way of the present invention over conventional techniques. For example, the present invention provides an easy to use method for training a process using more than one processing technique. Further, the invention can be used with a wide variety of substances, e.g., chemicals, fluids, biological materials, food products, plastic products, household goods. Additionally, the present invention can remove a need for human intervention in deciding which variables that describe a system or process are important or not important. Depending upon the embodiment, one or more of these benefits may be achieved. These and other benefits will be described in more throughout the present specification and more particularly below.

Various additional objects, features and advantages of the present invention can be more fully appreciated with reference to the detailed description and accompanying drawings that follow.

DETAILED DESCRIPTION OF THE INVENTION AND PREFERRED EMBODIMENTS

Figure 1:
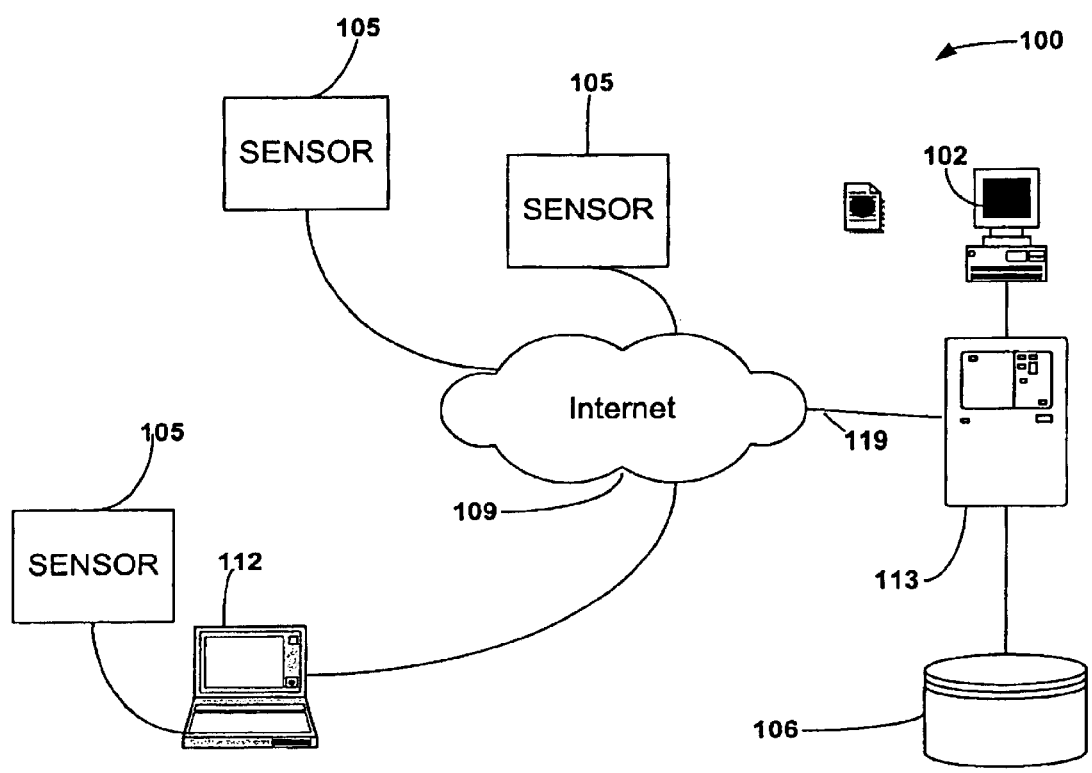
FIG. 1 is a simplified diagram of an environmental information analysis system according to an embodiment of the present invention.

FIG. 1 is a simplified diagram of an environmental information analysis system 100 according to an embodiment of the present invention. This diagram is merely an example, which should not limit the scope of the claims herein. One of ordinary skill in the art would recognize many other variations, modifications, and alternatives. As shown, the system 100 includes a variety of elements such as a wide area network 109 such as, for example, the Internet, an intranet, or other type of network. Connected to the wide area network 109 is an information server 113, with terminal 102 and database 106. The wide area network allows for communication of other computers such as a client unit 112. Client can be configured with many different hardware components and can be made in many dimensions, styles and locations (e.g., laptop, palmtop, pen, server, workstation and mainframe).

Terminal 102 is connected to server 113. This connection can be by a network such as Ethernet, asynchronous transfer mode, IEEE standard 1553 bus, modem connection, universal serial bus, etc. The communication link need not be a wire but can be infrared, radio wave transmission, etc. Server 113 is coupled to the Internet 109. The Internet is shown symbolically as a cloud or a collection of server routers, computers, and other devices 109. The connection to server is typically by a relatively high bandwidth transmission medium such as a T1 or T3 line, but can also be others.

In certain embodiments, Internet server 113 and database 106 store information and disseminate it to consumer computers e.g. over wide area network 109. The concepts of "client" and "server," as used in this application and the industry, are very loosely defined and, in fact, are not fixed with respect to machines or software processes executing on the machines. Typically, a server is a machine e.g. or process that is providing information to another machine or process, i.e., the "client," e.g., that requests the information. In this respect, a computer or process can be acting as a client at one point in time (because it is requesting information) and can be acting as a server at another point in time (because it is providing information). Some computers are consistently referred to as "servers" because they usually act as a repository for a large amount of information that is often requested. For example, a WEB site is often hosted by a server computer with a large storage capacity, high-speed processor and Internet link having the ability to handle many high-bandwidth communication lines.

In a specific embodiment, the network is also coupled to a plurality of sensing devices 105. Each of these sensing devices can be coupled directly to the network or through a client computer, such as client 112. Sensing devices 105 may be connected to a device such as a Fieldbus or CAN that is connected to the Internet. Alternatively, sensing devices 105 may be in wireless communication with the Internet.

Each of the sensing devices can be similar or different, depending upon the application. Each of the sensing devices is preferably an array of sensing elements for acquiring olfactory information from fluid substances, e.g., liquid, vapor, liquid/vapor. Once the information is acquired, each of the sensing devices transfers the information to server 113 for processing purposes. In the present invention, the process is performed for classifying or identifying one or more substances using the information that includes multi-dimensional data. Details of the processing hardware are shown below and illustrated by the Figs.

Figure 2:
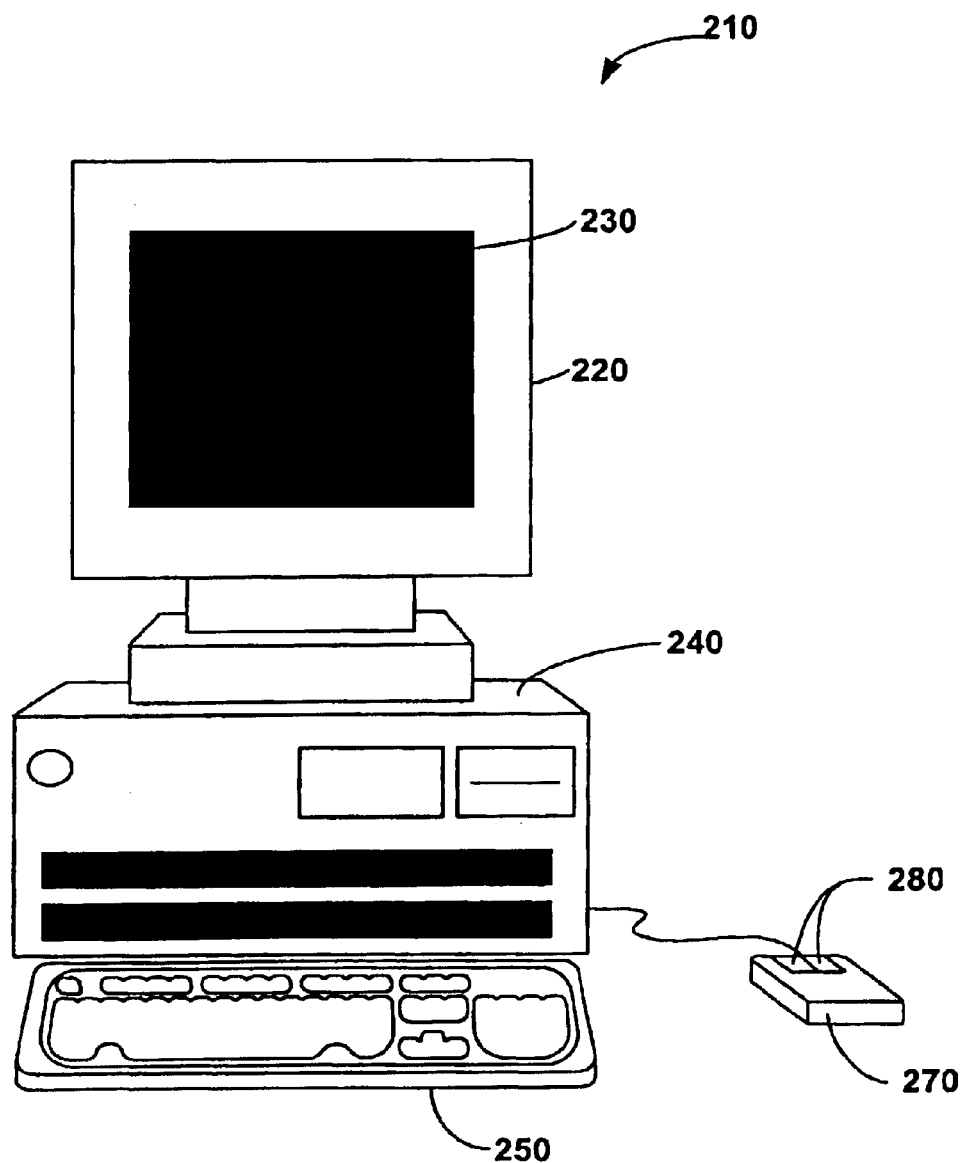
FIGS. 2 to 2A are simplified diagrams of computing device for processing information according to an embodiment of the present invention.

FIG. 2 is a simplified diagram of a computing device for processing information according to an embodiment of the present invention. This diagram is merely an example, which should not limit the scope of the claims herein. One of ordinary skill in the art would recognize many other variations, modifications, and alternatives. Embodiments according to the present invention can be implemented in a single application program such as a browser, or can be implemented as multiple programs in a distributed computing environment, such as a workstation, personal computer or a remote terminal in a client server relationship. FIG. 2 shows computer system 210 including display device 220, display screen 230, cabinet 240, keyboard 250, and mouse 270. Mouse 270 and keyboard 250 are representative "user input devices." Mouse 270 includes buttons 280 for selection of buttons on a graphical user interface device. Other examples of user input devices are a touch screen, light pen, track ball, data glove, microphone, and so forth. FIG. 2 is representative of but one type of system for embodying the present invention. It will be readily apparent to one of ordinary skill in the art that many system types and configurations are suitable for use in conjunction with the present invention. In a preferred embodiment, computer system 210 includes a Pentium™ class based computer, running Windows™ NT operating system by Microsoft Corporation. However, the apparatus is easily adapted to other operating systems and architectures by those of ordinary skill in the art without departing from the scope of the present invention.

As noted, mouse 270 can have one or more buttons such as buttons 280. Cabinet 240 houses familiar computer components such as disk drives, a processor, storage device, etc. Storage devices include, but are not limited to, disk drives, magnetic tape, solid state memory, bubble memory, etc. Cabinet 240 can include additional hardware such as input/output (I/O) interface cards for connecting computer system 210 to external devices external storage, other computers or additional peripherals, which are further described below.

Figure 2A:
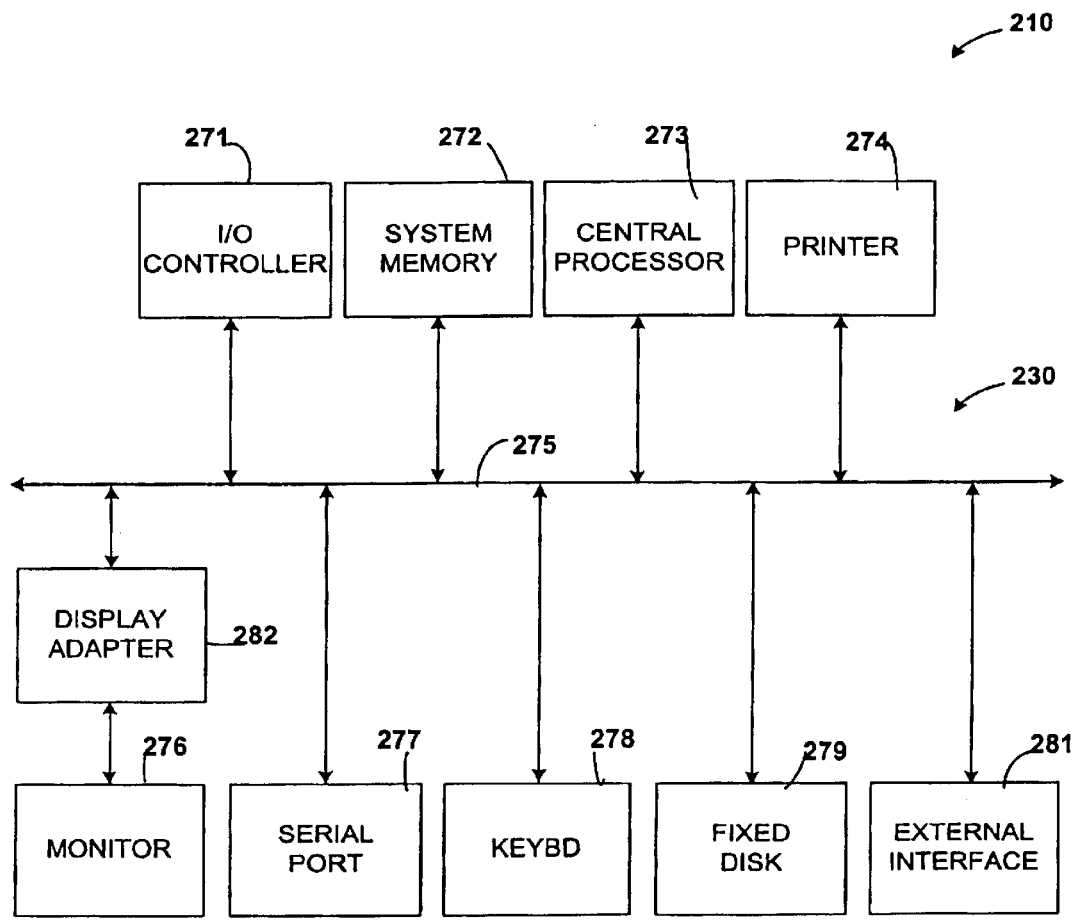

FIG. 2A is an illustration of basic subsystems in computer system 210 of FIG. 2. This diagram is merely an illustration and should not limit the scope of the claims herein. One of ordinary skill in the art will recognize other variations, modifications, and alternatives. In certain embodiments, the subsystems are interconnected via a system bus 275. Additional subsystems such as a printer 274, keyboard 278, fixed disk 279, monitor 276, which is coupled to display adapter 282, and others are shown. Peripherals and input/output (I/O) devices, which couple to I/O controller 271, can be connected to the computer system by any number of means known in the art, such as serial port 277. For example, serial port 277 can be used to connect the computer system to a modem 281, which in turn connects to a wide area network such as the Internet, a mouse input device, or a scanner. The interconnection via system bus allows central processor 273 to communicate with each subsystem and to control the execution of instructions from system memory 272 or the fixed disk 279, as well as the exchange of information between subsystems. Other arrangements of subsystems and interconnections are readily achievable by those of ordinary skill in the art. System memory, and the fixed disk are examples of tangible media for storage of computer programs, other types of tangible media include floppy disks, removable hard disks, optical storage media such as CD-RMOS and bar codes, and semiconductor memories such as flash memory, read-only-memories (ROM), and battery backed memory.

Figure 3:
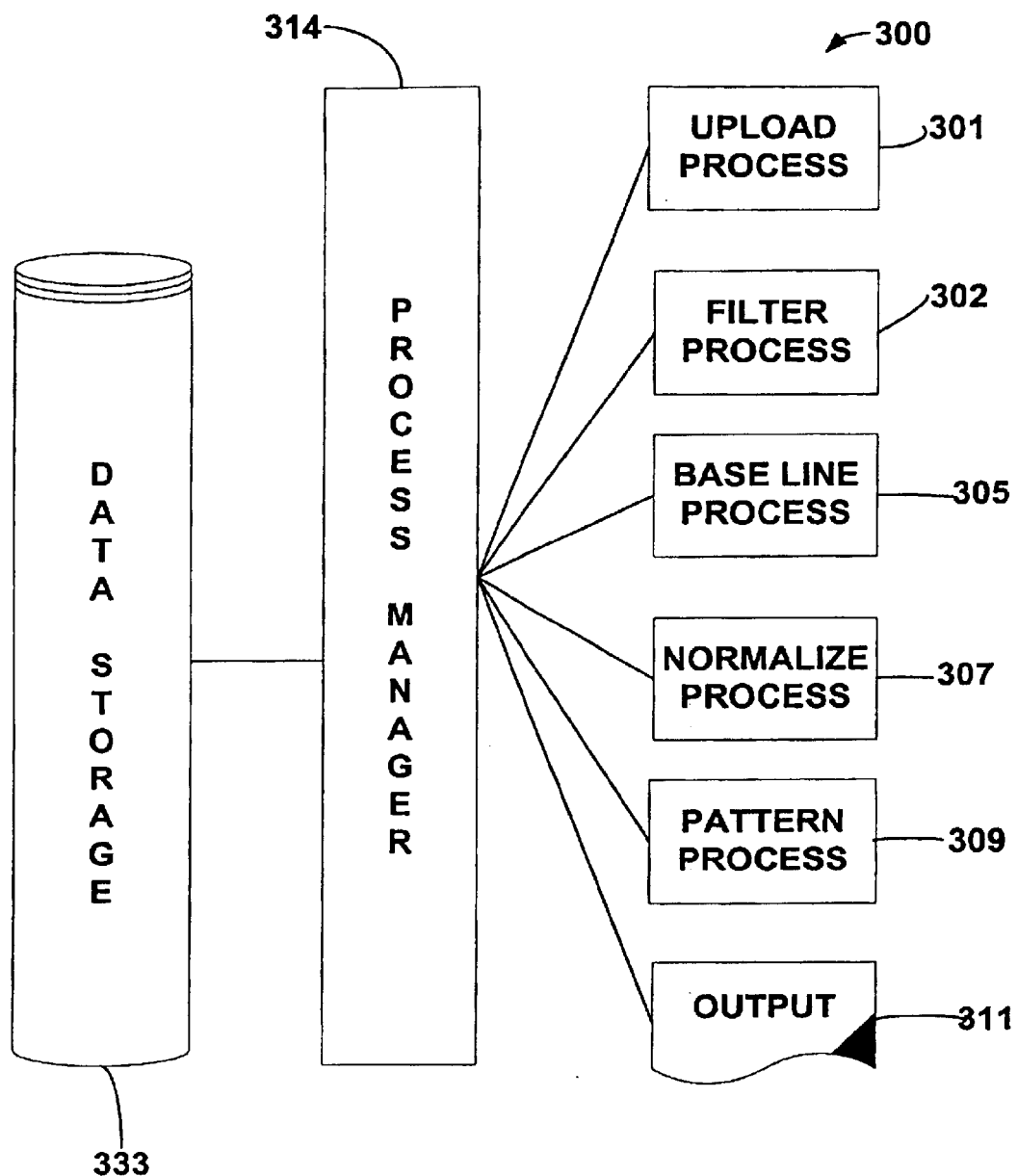
FIG. 3 is a simplified diagram of computing modules for processing information according to an embodiment of the present invention.

FIG. 3 is a simplified diagram of computing modules 300 in a system for processing information according to an embodiment of the present invention This diagram is merely an example which should not limit the scope of the claims herein. One of ordinary skill in the art would recognize many other variations, modifications, and alternatives. As shown, the computing modules 300 include a variety of processes, which couple to a process manager 314. The processes include an upload process 301, a filter process 302, a baseline process 305, a normalization process 307, a pattern process 309, and an output process 311. Other processes can also be included. Process manager also couples to data storage device 333 and oversees the processes. These processes can be implemented in software, hardware, firmware, or any combination of these in any one of the hardware devices, which were described above, as well as others.

The upload process takes data from the acquisition device and uploads them into the main process manager 314 for processing. Here, the data are in electronic form. In embodiments where the data has been stored in data storage, they are retrieved and then loaded into the process. Preferably, the data can be loaded onto workspace to a text file or loaded into a spreadsheet for analysis. Next, the filter process 302 filters the data to remove any imperfections. As merely an example, data from the present data acquisition device are often accompanied with glitches, high frequency noise, and the like. Here, the signal to noise ratio is often an important consideration for pattern recognition especially when concentrations of analytes are low, exceedingly high, or not within a predefined range of windows according to some embodiments. In such cases, it is desirable to boost the signal to noise ratio using the present digital filtering technology. Examples of such filtering technology includes, but is not limited to a Zero Phase Filter, an Adaptive Exponential Moving Average Filter, and a Savitzky-Golay Filter, which will be described in more detail below.

The data go through a baseline correction process 305. Depending upon the embodiment, there can be many different ways to implement a baseline correction process. Here, the baseline correction process finds response peaks, calculates $\Delta R/R$, and plots the $\Delta R/R$ verses time stamps, where the data have been captured. It also calculates maximum $\Delta R/R$ and maximum slope of $\Delta R/R$ for further processing. Baseline drift is often corrected by way of the present process. The main process manager also oversees that data traverse through the normalization process 307. In some embodiments, normalization is a row wise operation. Here, the process uses a so-called area normalization. After such normalization method, the sum of data along each row is unity. Vector length normalization is also used, where the sum of data squared of each row equals unity.

Next, the method performs a main process for classifying each of the substances according to each of their characteristics in a pattern recognition process. The pattern recognition process uses more than one algorithm, which are known, are presently being developed, or will be developed in the future. The process is used to find weighting factors for each of the characteristics to ultimately determine an identifiable pattern to uniquely identify each of the substances. That is, descriptors are provided for each of the substances. Examples of some algorithms are described throughout the present specification. Also shown is the output module 311. The output module is coupled to the process manager. The output module provides for the output of data from any one of the above processes as well as others. The output module can be coupled to one of a plurality of output devices. These devices include, among others, a printer, a display, and a network interface card. The present system can also include other modules. Depending upon the embodiment, these and other modules can be used to implement the methods according to the present invention.

The above processes are merely illustrative. The processes can be performed using computer software or hardware or a combination of hardware and software. Any of the above processes can also be separated or be combined, depending upon the embodiment. In some cases, the processes can also be changed in order without limiting the scope of the invention claimed herein. One of ordinary skill in the art would recognize many other variations, modifications, and alternatives.

Figure 3A:
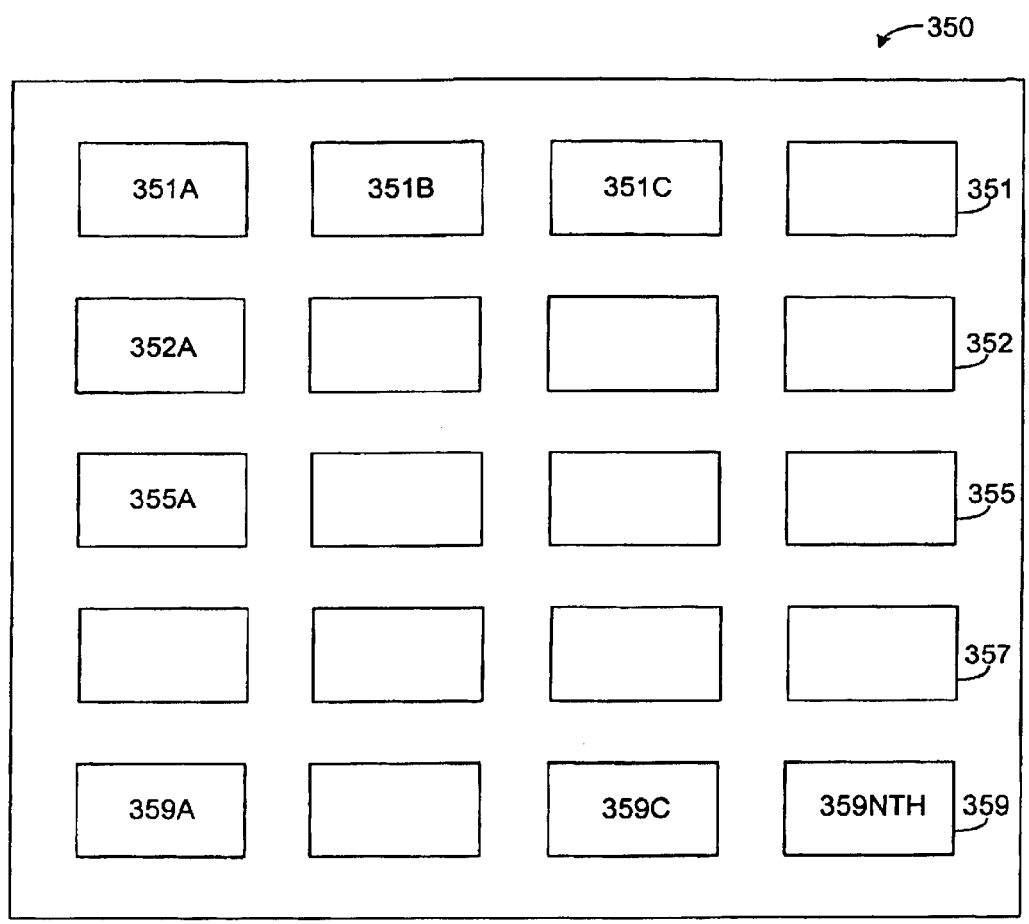
FIG. 3A is a simplified diagram of a capturing device for processing information according to an embodiment of the present invention.

FIG. 3A is a simplified diagram of a top-view 350 of an information-capturing device according to an embodiment of the present invention. This diagram is merely an example, which should not limit the scope of the claims herein. One of ordinary skill in the art would recognize many other variations, modifications, and alternatives. As shown, the top view diagram includes an array of sensors, 351A, 351B, 351C, 359nth. The array is arranged in rows 351, 352, 355, 357, 359 and columns, which are normal to each other. Each of the sensors has an exposed surface for capturing, for example, olfactory information from fluids, e.g., liquid and/or vapor. The diagram shown is merely an example. Details of such information-capturing device are provided in U.S. application Ser. No. 09/548,948 and U.S. Pat. No. 6,085,576, commonly assigned, and hereby incorporated by reference for all purposes. Other devices are commercially available from Osmetech, Hewlett Packard, Alpha-MOS, or other companies.

Although the above has been described in terms of a capturing device for fluids including liquids and/or vapors, there are many other types of capturing devices. For example, other types of information capturing devices for converting an intrinsic or extrinsic characteristic to a measurable parameter can be used. These information capturing devices include, among others, pH monitors, temperature measurement devices, humidity devices, pressure sensors, flow measurement devices, chemical detectors, velocity measurement devices, weighting scales, length measurement devices, color identification, and other devices. These devices can provide an electrical output that corresponds to measurable parameters such as pH, temperature, humidity, pressure, flow, chemical types, velocity, weight, height, length, and size.

In some aspects, the present invention can be used with at least two sensor arrays. The first array of sensors comprises at least two sensors (e.g., three, four, hundreds, thousands, millions or even billions) capable of producing a first response in the presence of a chemical stimulus. Suitable chemical stimuli capable of detection include, but are not limited to, a vapor, a gas, a liquid, a solid, an odor or mixtures thereof. This aspect of the device comprises an electronic nose. Suitable sensors comprising the first array of sensors include, but are not limited to conducting/nonconducting regions sensor, a SAW sensor, a quartz microbalance sensor, a conductive composite sensor, a chemiresistor, a metal oxide gas sensor, an organic gas sensor, a MOSFET, a piezoelectric device, an infrared sensor, a sintered metal oxide sensor, a Pd-gate MOSFET, a metal FET structure, a electrochemical cell, a conducting polymer sensor, a catalytic gas sensor, an organic semiconducting gas sensor, a solid electrolyte gas sensor, and a piezoelectric quartz crystal sensor. It will be apparent to those of skill in the art that the electronic nose array can be comprises of combinations of the foregoing sensors. A second sensor can be a single sensor or an array of sensors capable of producing a second response in the presence of physical stimuli. The physical detection sensors detect physical stimuli. Suitable physical stimuli include, but are not limited to, thermal stimuli, radiation stimuli, mechanical stimuli, pressure, visual, magnetic stimuli, and electrical stimuli.

Thermal sensors can detect stimuli which include, but are not limited to, temperature, heat, heat flow, entropy, heat capacity, etc. Radiation sensors can detect stimuli that include, but are not limited to, gamma rays, X-rays, ultraviolet rays, visible, infrared, microwaves and radio waves. Mechanical sensors can detect stimuli which include, but are not limited to, displacement, velocity, acceleration, force, torque, pressure, mass, flow, acoustic wavelength, and amplitude. Magnetic sensors can detect stimuli that include, but are not limited to, magnetic field, flux, magnetic moment, magnetization, and magnetic permeability. Electrical sensors can detect stimuli which include, but are not limited to, charge, current, voltage, resistance, conductance, capacitance, inductance, dielectric permittivity, polarization and frequency.

In certain embodiments, thermal sensors are suitable for use in the present invention that include, but are not limited to, thermocouples, such as a semiconducting thermocouples, noise thermometry, thermoswitches, thermistors, metal thermoresistors, semiconducting thermoresistors, thermodiodes, thermotransistors, calorimeters, thermometers, indicators, and fiber optics.

In other embodiments, various radiation sensors are suitable for use in the present invention that include, but are not limited to, nuclear radiation microsensors, such as scintillation counters and solid state detectors, ultra-violet, visible and near infrared radiation microsensors, such as photoconductive cells, photodiodes, phototransistors, infrared radiation microsensors, such as photoconductive IR sensors and pyroelectric sensors.

In certain other embodiments, various mechanical sensors are suitable for use in the present invention and include, but are not limited to, displacement microsensors, capacitive and inductive displacement sensors, optical displacement sensors, ultrasonic displacement sensors, pyroelectric, velocity and flow microsensors, transistor flow microsensors, acceleration microsensors, piezoresistive microaccelerometers, force, pressure and strain microsensors, and piezoelectric crystal sensors.

In certain other embodiments, various chemical or biochemical sensors are suitable for use in the present invention and include, but are not limited to, metal oxide gas sensors, such as tin oxide gas sensors, organic gas sensors, chemocapacitors, chemodiodes, such as inorganic Schottky device, metal oxide field effect transistor (MOSFET), piezoelectric devices, ion selective FET for pH sensors, polymeric humidity sensors, electrochemical cell sensors, pellistors gas sensors, piezoelectric or surface acoustical wave sensors, infrared sensors, surface plasmon sensors, and fiber optical sensors.

Various other sensors suitable for use in the present invention include, but are not limited to, sintered metal oxide sensors, phthalocyanine sensors, membranes, Pd-gate MOSFET, electrochemical cells, conducting polymer sensors, lipid coating sensors and metal FET structures. In certain preferred embodiments, the sensors include, but are not limited to, metal oxide sensors such as a Tuguchi gas sensors, catalytic gas sensors, organic semiconducting gas sensors, solid electrolyte gas sensors, piezoelectric quartz crystal sensors, fiber optic probes, a micro-electro-mechanical system device, a micro-opto-electro-mechanical system device and Langmuir-Blodgett films.

Additionally, the above description in terms of specific hardware is merely for illustration. It would be recognized that the functionality of the hardware be combined or even separated with hardware elements and/or software. The functionality can also be made in the form of software, which can be predominantly software or a combination of hardware and software. One of ordinary skill in the art would recognize many variations, alternatives, and modifications. Details of methods according to the present invention are provided below.

A method using digital olfaction information for populating a database for identification or classification purposes according to the present invention may be briefly outlined as follows:

1. Acquire olfactory data, where the data are for one or more substances, each of the substances having a plurality of distinct characteristics;

2. Convert olfactory data into electronic form;

3. Provide olfaction data in electronic form (e.g., text, normalized data from an array of sensors) for classification or identification;

4. Load the data into a first memory by a computing device;

5. Retrieve the data from the first memory;

6. Remove first noise levels from the data using one or more filters;

7. Correct data to a baseline for one or more variables such as drift, temperature, humidity, etc.;

8. Normalize data using a baseline;

9. Reject one or more of the plurality of distinct characteristics from the data;

10. Perform one or more pattern recognition methods on the data;

11. Classify the one or more substances based upon the pattern recognition methods to form multiple classes that each corresponds to a different substance;

12. Determine optimized (or best general fit) pattern recognition method via cross validation process;

13. Store the classified substances into a second memory for further analysis; and 14. Perform other steps, as desirable.

The above sequence of steps is merely an example of a way to teach or train the present method and system. The present example takes more than one different substance, where each substance has a plurality of characteristics, which are capable of being detected by sensors. Each of these characteristics are measured, and then fed into the present method to create a training set. The method includes a variety of data processing techniques to provide the training set. Depending upon the embodiment, some of the steps may be separated even further or combined. Details of these steps are provided below according to Figs.

Figure 4A:
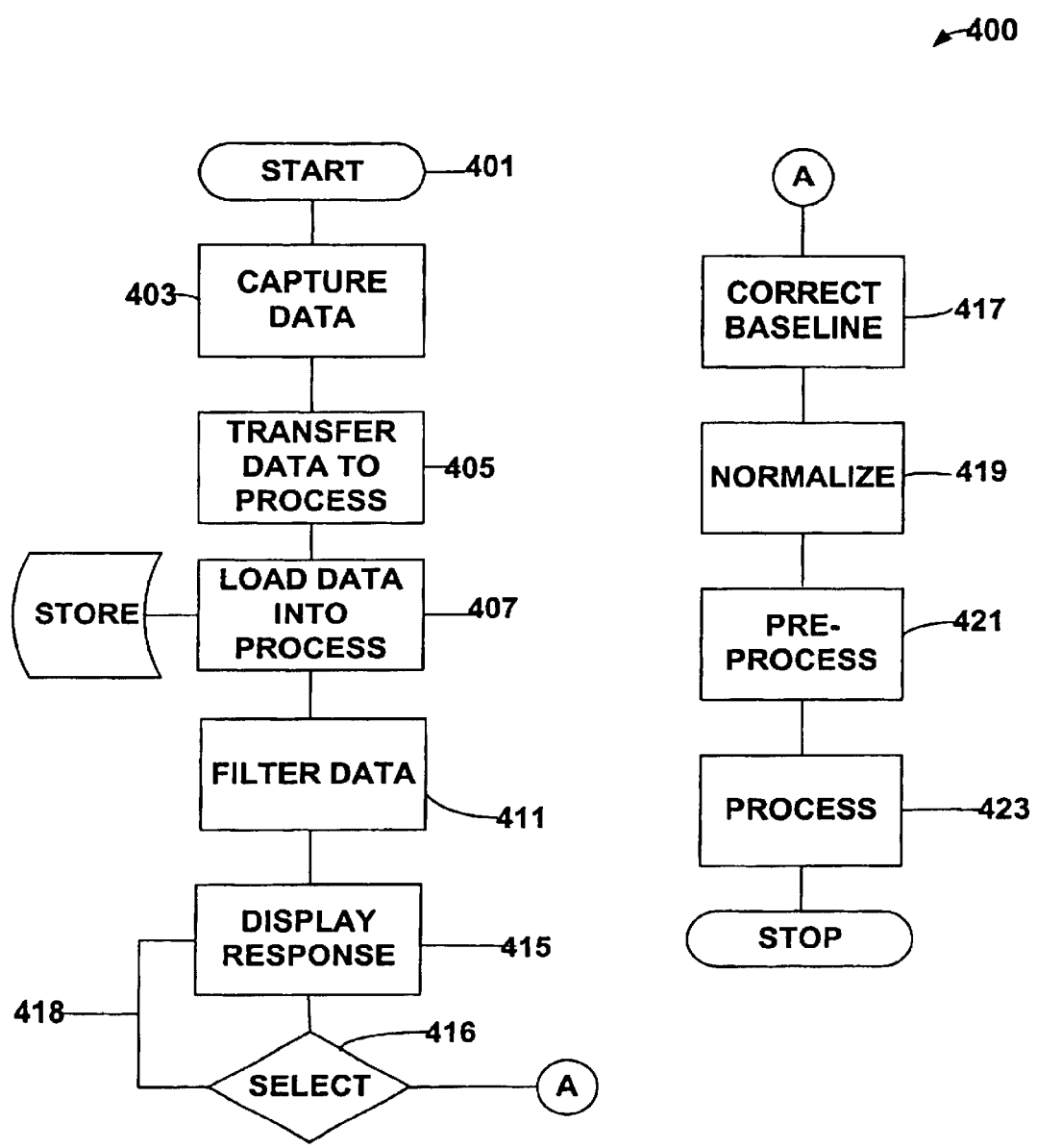
FIGS. 4A to 4E are simplified diagrams of methods according to embodiments of the present invention.
Figure 4B:
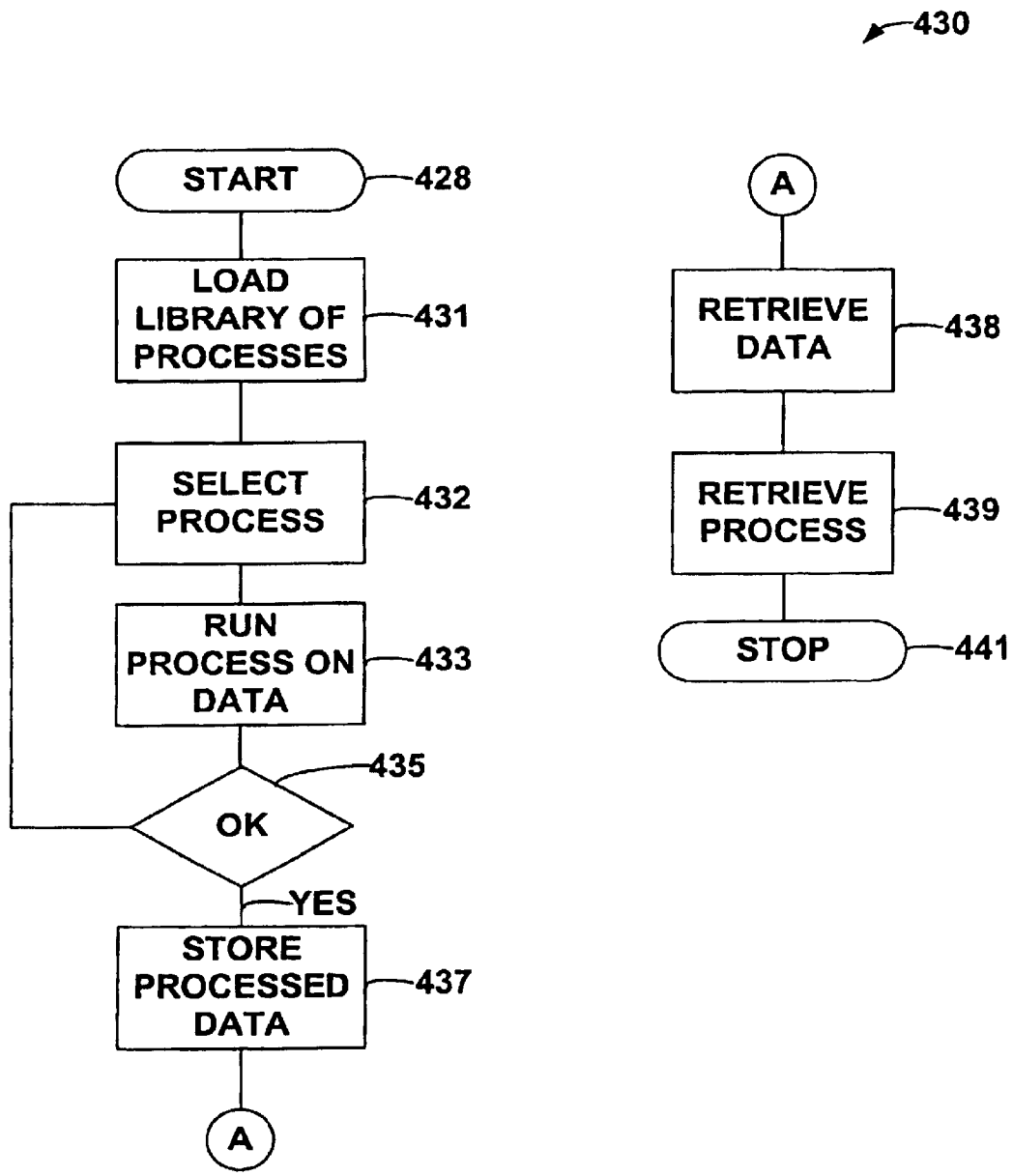

FIGS. 4A to 4B are simplified diagrams of methods according to embodiments of the present invention. These diagrams are merely examples, which should not limit the scope of the claims herein. One of ordinary skill in the art would recognize many other variations, modifications, and alternatives. As shown, the present method 400 begins at start, step 401. The method then captures data (step 403) from a data acquisition device. The data acquisition device can be any suitable device for capturing either intrinsic or extrinsic information from a substance. As merely an example, the present method uses a data acquisition device for capturing olfactory information. The device has a plurality of sensors, which convert a scent or olfaction print into an artificial or electronic print. In a specific embodiment, such data acquisition device is disclosed in WO 99/47905, WO 00/52444 and WO 00/79243 all commonly assigned and hereby incorporated by reference for all purposes. Those of skill in the art will know of other devices including other electronic noses suitable for use in the present invention. In a specific embodiment, the present invention captures olfactory information from a plurality of different liquids, e.g., isopropyl alcohol, water, toluene. The olfactory information from each of the different liquids is characterized by a plurality of measurable characteristics, which are acquired by the acquisition device. Each different liquid including the plurality of measurable characteristics can be converted into an electronic data form for use according to the present invention. Some of these characteristics were previously described, but can also include others.

Next, the method transfers the electronic data, now in electronic form, to a computer-aided process (step 405). The computer-aided process may be automatic and/or semiautomatic depending upon the application. The computer-aided process can store the data into memory, which is coupled to a processor. When the data is ready for use, the data is loaded into the process, step 407. In embodiments where the data has been stored, they are retrieved and then loaded into the process. Preferably, the data can be loaded onto workspace to a text file or loaded into a spreadsheet for analysis. Here, the data can be loaded continuously and automatically, or be loaded manually, or be loaded and monitored continuously to provide real time analysis.

The method filters the data (step 411) to remove any imperfections. As merely an example, data from the present data acquisition device are often accompanied with glitches, high frequency noise, and the like. Here, the signal to noise ratio is often an important consideration for pattern recognition especially when concentrations of analytes are low, exceedingly high, or not within a predefined range of windows according to some embodiments. In such cases, it is desirable to boost the signal to noise ratio using the present digital filtering technology. Examples of such filtering technology includes, but is not limited to, a Zero Phase Filter, an Adaptive Exponential Moving Average Filter, and a Savitzky-Golay Filter, which will be described in more detail below.

Optionally, the filtered responses can be displayed, step 415. Here, the present method performs more than one of the filtering techniques to determine which one provides better results. By way of the present method, it is possible to view the detail of data preprocessing. The method displays outputs (step 415) for each of the sensors, where signal to noise levels can be visually examined. Alternatively, analytical techniques can be used to determine which of the filters worked best. Each of the filters are used on the data, step 416 via branch 418. Once the desired filter has been selected, the present method goes to the next step.

The method performs a baseline correction step (step 417). Depending upon the embodiment, there can be many different ways to implement a baseline correction method. Here, the baseline correction method finds response peaks, calculates $\Delta R/R$, and plots the $\Delta R/R$ verses time stamps, where the data have been captured. It also calculates maximum $\Delta R/R$ and maximum slope of $\Delta R/R$ for further processing. Baseline drift is often corrected by way of the present step. Once baseline drift has been corrected, the present method undergoes a normalization process, although other processes can also be used. Here, $\Delta R/R$ can be determined using one of a plurality of methods, which are known, if any, or developed according to the present invention. As will be apparent to those of skill in the art, although in the example resistance is used, the method can use impedance, voltage, capacitance and the like as a sensor response.

Figure 4C:
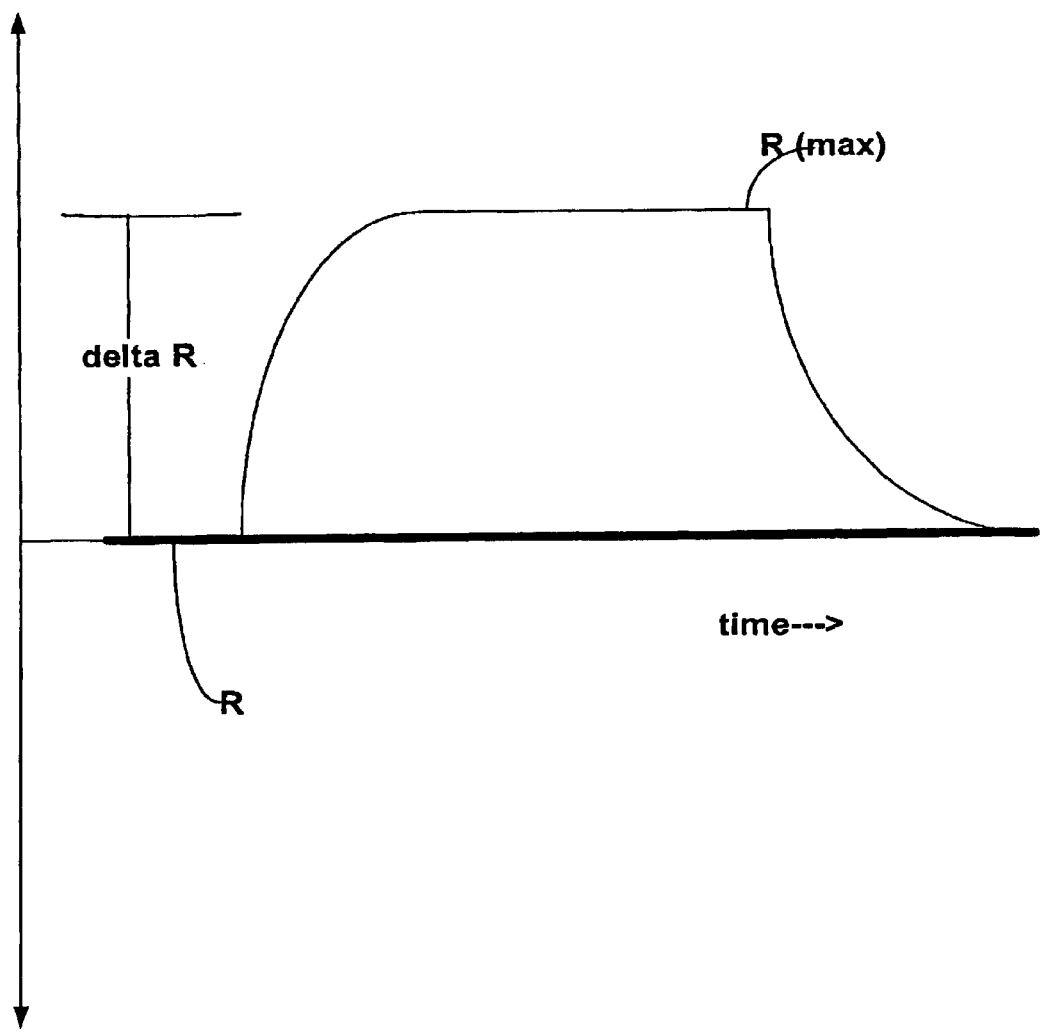

As merely an example, FIG. 4C illustrates a simplified plot of a signal and various components used in the calculation of $\Delta R/R$, which can be used depending upon the embodiment. This diagram is merely an illustration, which should not limit the scope of the claims herein. One of ordinary skill in the art would recognize many other variations, modifications, and alternatives. As shown, the diagram shows a pulse, which is plotted along a time axis, which intersects a voltage, for example. The diagram includes a $\Delta R$ (i.e., delta R), which is defined between R and R(max). As merely an example, $\Delta R/R$ is defined by the following expression:

$$\Delta R/R = (R(\max) - R(0))/R$$

wherein: $\Delta R$ is defined by the average difference between a baseline value $R(0)$ and $R(\max)$; $R(\max)$ is defined by a maximum value of R; $R(0)$ is defined by an initial value of R; and R is defined as a variable or electrical measurement of resistance from a sensor, for example.

This expression is merely an example, the term $\Delta R/R$ could be defined by a variety of other relationships. Here, $\Delta R/R$ has been selected in a manner to provide an improved signal to noise ratio for the signals from the sensor, for example. There can be many other relationships that define $\Delta R/R$, which may be a relative relation in another manner. Alternatively, $\Delta R/R$ could be an absolute relationship or a combination of a relative relationship and an absolute relationship. Of course, one of ordinary skill in the art would provide many other variations, alternatives, and modifications.

As noted, the method includes a normalization step, step 419. In some embodiments, normalization is a row wise operation. Here, the method uses a so-called area normalization. After such normalization method, the sum of data along each row is unity. Vector length normalization is also used, where the sum of data squared of each row equals unity.

As shown by step 421, the method may next perform certain preprocessing techniques. Preprocessing can be employed to eliminate the effect on the data of inclusion of the mean value in data analysis, or of the use of particular units of measurement, or of large differences in the scale of the different data types received. Examples of such preprocessing techniques include mean centering and auto scaling. Preprocessing techniques utilized for other purposes include for example, smoothing, outlier rejection, drift monitoring, and others. Some of these techniques will be described later. Once preprocessing has been completed, the method performs a detailed processing technique.

Next, the method performs a main process for classifying each of the substances according to each of their characteristics, step 423. Here, the present method performs a pattern recognition process, such as the one illustrated by the simplified diagram in FIG. 4B. This diagram is merely an example, which should not limit the scope of the claims herein.

As shown, method 430 begins with start, step 428. The method queries a library, including a plurality of pattern recognition algorithms (e.g., Table I below), and loads (step 431) one or more of the algorithms in memory to be used. The method selects the one algorithm, step 432, and runs the data through the algorithm, step 433. In a specific embodiment, the pattern recognition process uses more than one algorithms, which are known, are presently being developed, or will be developed in the future. The process is used to find weighting factors based upon descriptors for each of the characteristics to ultimately determine an identifiable pattern to uniquely identify each of the substances. The present method runs the data, which have been preprocessed, through each of the algorithms. Representative algorithms are set forth in Table I.

TABLE I

| PCA | Principal Components Analysis |
| --- | --- |
| HCA | Hierarchical Cluster Analysis |
| KNN CV | K Nearest Neighbor Cross Validation |
| KNN Prd | K Nearest Neighbor Prediction |
| SIMCA CV | SIMCA Cross Validation |
| SIMCA Prd | SIMCA Prediction |
| Canon CV | Canonical Discriminant Analysis and Cross Validation |
| Canon Prd | Canonical Discriminant Prediction |
| Fisher CV | Fisher Linear Discriminant Analysis and Cross Validation |
| Fisher Prd | Fisher Linear Discriminant Prediction |

PCA and HCA, are unsupervised learning methods. They can be used for investigating training data and finding the answers of:

TABLE II

| I. | How many principal components will cover the most of variances? |
| --- | --- |
| II. | How many principal components to choose? |
| III. | How do the loading plots look? |
| IV. | How do the score plots look? |
| V. | How are the scores separated among the classes? |
| VI. | How are the clusters grouped in their classes? |
| VII. | How much are the distances among the clusters? |

The other four algorithms, KNN CV, SIMCA CV, Canon CV, and Fisher CV, are supervised learning methods used when the goal is to construct models to be used to classify future samples. These algorithms will do cross validation, find the optimum number of parameters, and build models.

Once the data has been run through the first algorithm, for example, the method repeats through a branch (step 435) to step 432 to another process. This process is repeated until one or more of the algorithms have been used to analyze the data. The process is repeated to try to find a desirable algorithm that provides good results with a specific preprocessing technique used to prepare the data. If all of the desirable algorithms have been used, the method stores (or has previously stored) (step 437) each of the results of the processes on the data in memory.

In a specific embodiment, the present invention provides a cross-validation technique. Here, an auto (or automatic) cross-validation algorithm has been implemented. The present technique uses cross-validation, which is an operation process used to validate models built with chemometrics algorithms based on training data set. During the process, the training data set is divided into calibration and validation subsets. A model is built with the calibration subset and is used to predict the validation subset. The training data set can be divided into calibration and validation subsets called "leave-one-out", i.e., take one sample out from each class to build a validation subset and use the rest samples to build a calibration subset. This process can be repeated using different subset until every sample in the training set has been included in one validation subset. The predicted results are stored in an array. Then, the correct prediction percentages (CPP) are calculated, and are used to validate the performance of the model. One of ordinary skill in the art would recognize other techniques for determining calibration and validation sets when performing either internal cross-validation or external cross-validation.

According to the present method, a cross-validation with one training data set can be applied to generally all the models built with different algorithms, such as K-Nearest Neighbor (KNN), SIMCA, Canonical Discriminant Analysis, and Fisher Linear Discriminant Analysis, respectively. The results of correct prediction percentages (CPP) show the performance differences with the same training data set but with different algorithms. Therefore, one can pick up the best algorithm according to the embodiment.

During the model building, there are several parameters and options to choose. To build the best model with one algorithm, cross-validation is also used to find the optimum parameters and options. For example, in the process of building a KNN model, cross-validation is used to validate the models built with different number of K, different scaling options, e.g., mean-centering or auto-scaling, and other options, e.g., with PCA or without PCA, to find out the optimum combination of K and other options. In an alternative embodiment, auto-cross-validation is implemented using a single push-button for ease in use. It automatically runs the processes mentioned above over all the (or any selected) algorithms with the training data set to determine the optimum combination of parameters, scaling options and algorithms.

The method also performs additional steps of retrieving data, step 438, and retrieving the process or algorithm, step 439. As noted, each of the processes can form a descriptor for each sample in the training set. Each of these descriptors can be stored and retrieved. Here, the method stores the raw data, the preprocessed data, the descriptors, and the algorithm used for the method for each algorithm used according to the present invention. The method stops at step 441.

The above sequence of steps is merely illustrative. The steps can be performed using computer software or hardware or a combination of hardware and software. Any of the above steps can also be separated or be combined, depending upon the embodiment. In some cases, the steps can also be changed in order without limiting the scope of the invention claimed herein. One of ordinary skill in the art would recognize many other variations, modifications, and alternatives.

An alternative method according to the present invention is briefly outlined as follows:
 1. Acquire raw data in voltages;
 2. Check baseline voltages;
 3. Filter;
 4. Calculate ΔR/R
 5. Determine Training set?
 6. If yes, find samples (may repeat process);
 7. Determine outlier?;
 8. If yes, remove bad data using, for example PCA;
 9. Find important sensors using importance index (individual filtering process);
 10. Normalize;
 11. Find appropriate pattering recognition process;
 12. Run each pattern recognition process;
 13. Display (optional);
 14. Find best fit out of each pattern recognition process;
 15. Compare against confidence factor;
 16. Perform other steps, as required.

The above sequence of steps is merely an example of a way to teach or train the present method and system according to an alternative embodiment. The present example takes more than one different substance, where each substance has a plurality of characteristics, which are capable of being detected by sensors or other sensing devices. Each of these characteristics is measured, and then fed into the present method to create a training set. The method includes a variety of data processing techniques to provide the training set. Depending upon the embodiment, some of the steps may be separated even further or combined. Details of these steps are provided below according to Figs.

Figure 4D:
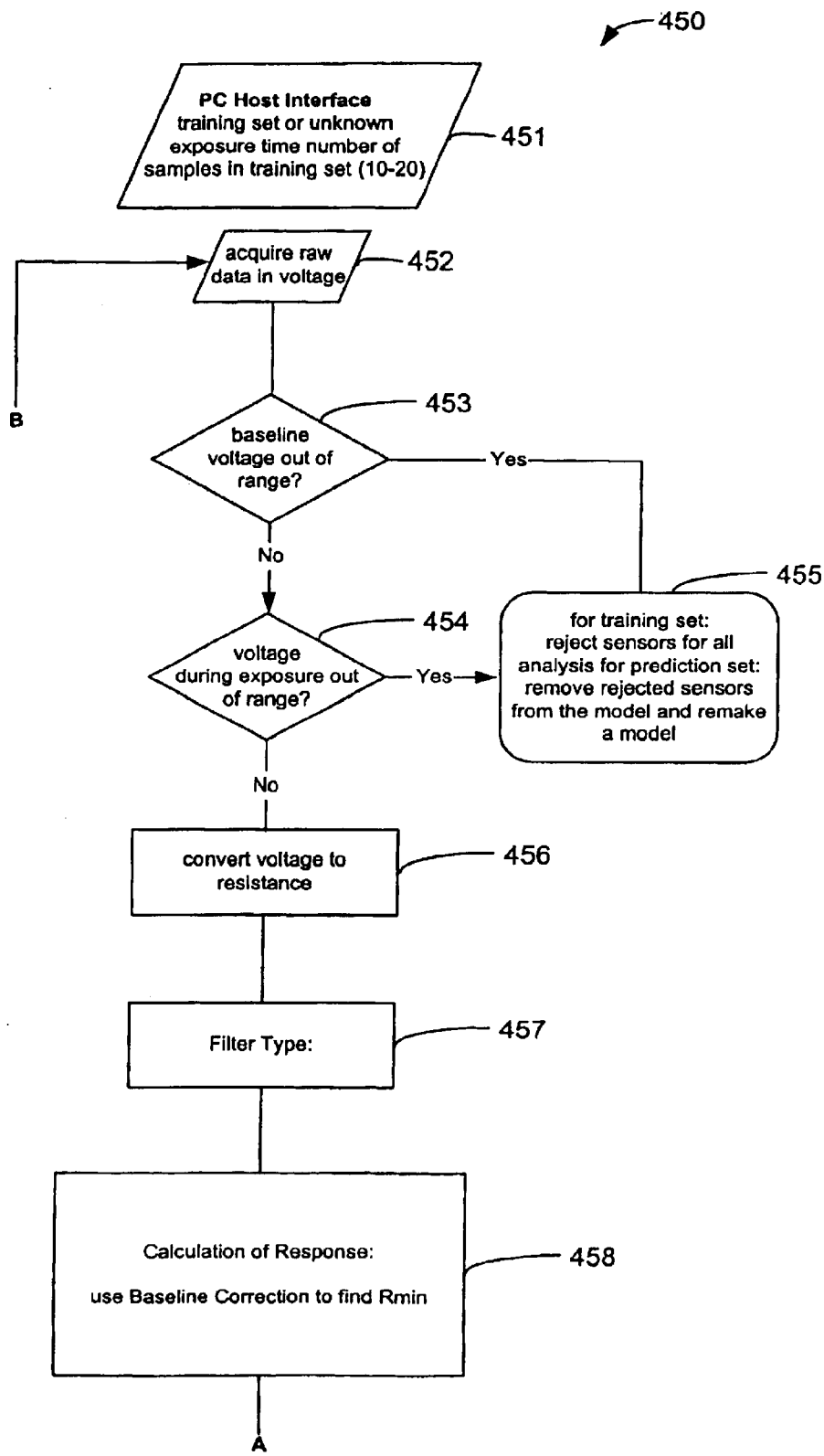
Figure 4E:
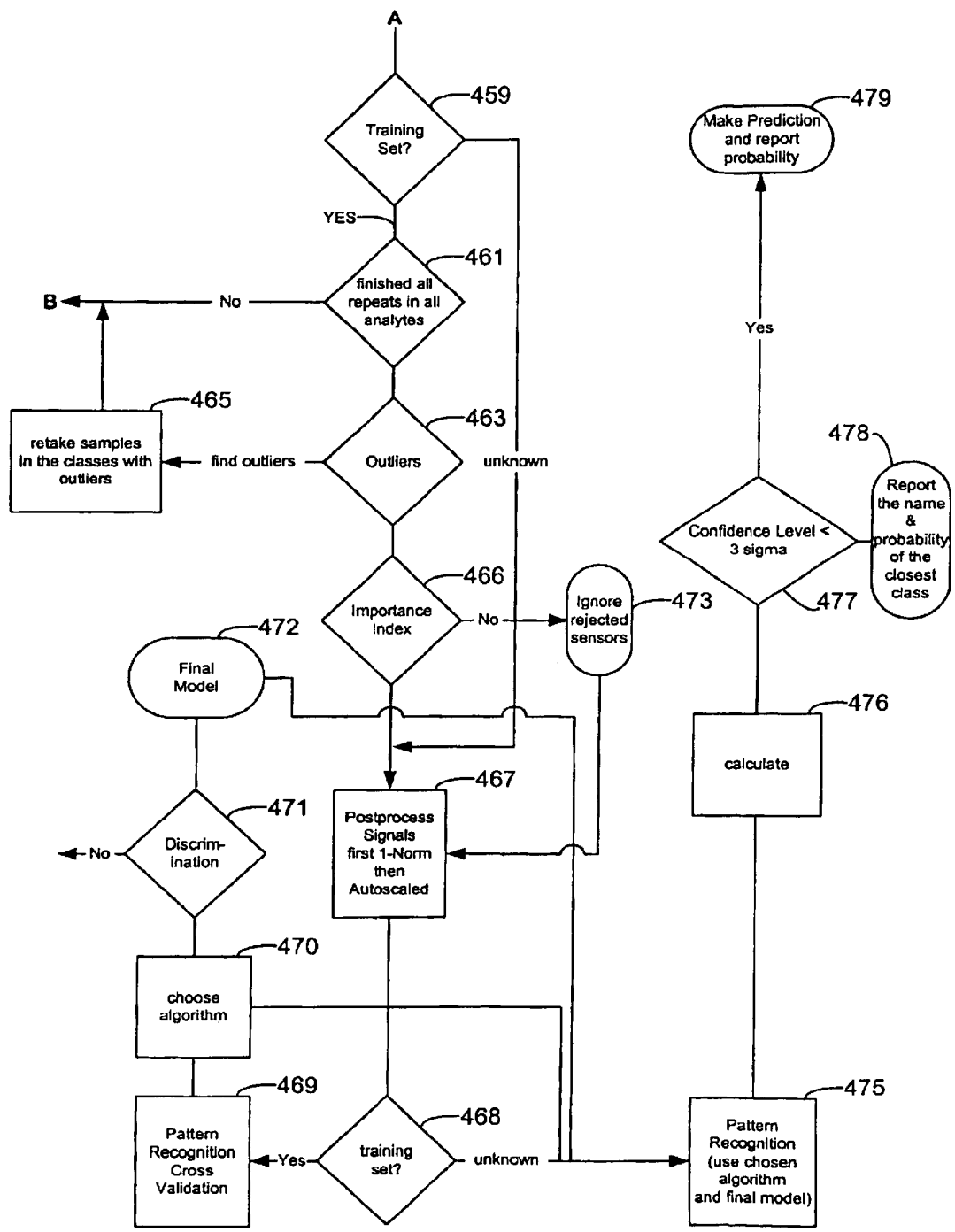

FIGS. 4D and 4E are simplified diagrams of methods according to embodiments of the present invention. These diagrams are merely examples, which should not limit the scope of the claims herein. One of ordinary skill in the art would recognize many other variations, modifications, and alternatives. As shown, the present method 450 begins at step 451. Here, the method begins at a personal computer host interface, where the method provides a training set of samples (which are each defined as a different class of material) to be analyzed or an unknown sample (once the training set has been processed). The training set can be derived from a plurality of different samples of fluids (or other substances or information). The samples can range in number from more than one to more than five or more than ten or more than twenty in some applications. The present method processes one sample at a time through the method that loops back to step 451 via the branch indicated by reference letter B, for example, from step 461, which will be described in more detail below.

In a specific embodiment, the method has captured data about the plurality of samples from a data acquisition device. Here, each of the samples form a distinct class of data according to the present invention. The data acquisition device can be any suitable device for capturing either intrinsic or extrinsic information from a substance. As merely an example, the present method uses a data acquisition device for capturing olfactory information. The device has a plurality of sensors or sensing devices, which convert a scent or olfaction print into an artificial or electronic print. In a specific embodiment, such data acquisition device is disclosed in WO 99/47905, WO 00/52444 and WO 00/79243 all commonly assigned and hereby incorporated by reference for all purposes. Those of skill in the art will know of other devices including other electronic noses suitable for use in the present invention. In a specific embodiment, the present invention captures olfactory information from a plurality of different liquids, e.g., isopropyl alcohol, water, toluene. The olfactory information from each of the different liquids is characterized by a plurality of measurable characteristics, which are acquired by the acquisition device. Each different liquid including the plurality of measurable characteristics can be converted into an electronic data form for use according to the present invention.

The method acquires the raw data from the sample in the training set often as a voltage measurement, step 452. The voltage measurement is often plotted as a function of time. In other embodiments, there are many other ways to provide the raw data. For example, the raw data can be supplied as a resistance, a current, a capacitance, an inductance, a binary characteristic, a quantized characteristic, a range value or values, and the like. Of course, the type of raw data used depends highly upon the application. In some embodiments, the raw data can be measured multiple times, where an average is calculated. The average can be a time weighted value, a mathematical weighted value, and others.

Next, the method checks the baseline voltages from the plurality of sensing devices used to capture information from the sample, as shown in step 453. The method can perform any of the baseline correction methods described herein, as well as others. Additionally, the method can merely check to see if each of the sensing devices has an output voltage within a predetermined range. If each of the sensing devices has an output voltage within a predetermined range, each of the sensing devices has a baseline voltage that is not out of range. Here, the method continues to the next step. Alternatively, the method goes to step 455, which rejects the sensing device that is outside of the predetermined voltage range, and then continues to the next step. In some embodiments, the sensing device that is outside of the range is a faulty or bad sensor, which should not be used for training or analysis purposes.

The method then determines if the measured voltage for each sensing device is within a predetermined range, step 454. Exposing the sensor to the sample provides the voltage for each sensor. The exposure can be made for a predetermined amount of time. Additionally, the exposure can be repeated and averaged, either by time or geometrically. The voltage is compared with a range or set of ranges, which often characterize the sensor for the exposure. If the exposed sensing device is outside of its predetermined range for the exposure, the method can reject (step 455) the sensor and proceed to the next step. The rejected sensor may be faulty or bad. Alternatively, if each of the sensing devices in, for example, the array of sensors is within a respective predetermined range, then the method continues to the next step, which will be discussed below.

The method can convert the voltage into a resistance value, step 456. Alternatively, the voltage can be converted to a capacitance, an inductance, an impedance, or other measurable characteristic. In some embodiments, the voltage is merely converted using a predetermined relationship for each of the sensing devices. Alternatively, there may be a look up table, which correlates voltages with resistances. Still further, there can be a mathematical relationship that correlates the voltage with the resistance.

The method then runs the data through one or more filters, step 457. The method filters the data to remove any imperfections, noise, and the like. As merely an example, data from the present data acquisition device are often accompanied with glitches, high frequency noise, and the like. Here, the signal to noise ratio is often an important consideration for pattern recognition especially when concentrations of analytes are low, exceedingly high, or not within a predefined range of windows according to some embodiments. In such cases, it is desirable to boost the signal to noise ratio using the present digital filtering technology. Examples of such filtering technology includes, but is not limited to a Zero Phase Filter, an Adaptive Exponential Moving Average Filter, and a Savitzky-Golay Filter.

The method runs a response on the data, step 458. Here, the method may perform a baseline correction step. Depending upon the embodiment, there can be many different ways to implement a baseline correction method. Here, the baseline correction method finds response peaks, calculates $\Delta R/R$, and plots the $\Delta R/R$ verses time stamps, where the data have been captured. It also calculates maximum $\Delta R/R$ and maximum slope of $\Delta R/R$ for further processing. Baseline drift is often corrected by way of the present step. Once baseline drift has been corrected, the present method undergoes a normalization process, although other processes can also be used. Here, $\Delta R/R$ can be determined using one of a plurality of methods, which are known, if any, or developed according to the present invention.

In the present embodiment, the method is for analyzing a training set of substances, step 459 (in FIG. 4E). The method then continues to step 461. Alternatively, the method skips to step 467, which will be described in one or more of the copending applications. If there is another substances in the training set to be analyzed (step 459), the method returns to step 452 via branch B, as noted above. Here, the method continues until each of the substances in the training set has been run through the process in the present preprocessing steps. The other samples will run through generally each of the above steps, as well as others, in some embodiments.

Next, the method goes to step 463. This step determines if any of the data has an outlier. In the present embodiment, the outlier is a data point, which does not provide any meaningful information to the method. Here, the outlier can be a data point that is outside of the noise level, where no conclusions can be made. The outlier is often thought of a data point that is tossed out due to statistical deviations or because of a special cause of variation. That is, lowest and highest data points can be considered as outliers in some embodiments. If outliers are found, step 463, the method can retake (step 465) samples, which are exposed to the sensing devices, that have the outliers. The samples that are retaken loop back through the process via the branch indicated by reference letter B. Outliers can be removed from the data in some embodiments.

The method also can uncover important sensors using an importance index (individual filtering process). Here, the method identifies which sensors do not provide any significant information by comparing a like sensor output with a like sensor output for each of the samples in the training set. If certain sensors are determined to have little influence in the results, these sensors are ignored (step 473) and then continues to the next step, as shown. Alternatively, if generally all sensors are determined to have some significance, the method continues to step 467.

Next, the method performs post processing procedures (step 467), as defined herein. The post processing procedures include, for example, a normalization step. In a specific embodiment, the normalization step scales the data to one or other reference value and then autoscales the data so that each sample value is referenced against each other. If the data is for the training step, step 468, the method continues to a pattern recognition cross-validation process, step 469, the cross validation process is used with step 470.

As described previously, the pattern recognition process uses more than one algorithm, for example from Table I, which are known, are presently being developed, or will be developed in the future. The process is used to find weighting factors for each of the characteristics to ultimately determine an identifiable pattern to uniquely identify each of the substances. The present method runs the data, which have been preprocessed, through each of the algorithms.

Once the best fit algorithm and model has been uncovered, the method goes through a discrimination test, step 471. In a specific embodiment, the method compares the results, e.g., fit of data against algorithm, combination of data and other preprocessing information, against confidence factor (if less than a certain number, this does not work). This step provides a final screen on the data, the algorithm used, the pre-processing methods, and other factors to see if everything just makes sense. If so, the method selects the final combination of techniques used according to an embodiment of the present invention.

The above sequence of steps is merely illustrative. The steps can be performed using computer software or hardware or a combination of hardware and software. Any of the above steps can also be separated or be combined, depending upon the embodiment. In some cases, the steps can also be changed in order without limiting the scope of the invention claimed herein. One of ordinary skill in the art would recognize many other variations, modifications, and alternatives.

EXAMPLE

To prove the principle and operation of the present invention, a computer software program was coded and used to implement aspects of the present invention. This program is merely an example, which should not unduly limit the scope of the claims herein. One of ordinary skill in the art would recognize many other variations, modifications, and alternatives. Here, a program package named "Simulation" has been written in MATLAB with a graphical user interface (GUI) to simulate the data input from chemical sensors, data preprocessing and pattern recognition so that users can try different algorithms to find the best method to meet a certain application. This procedure includes many recommendations about details of operation to help users perform their specific task. It is demonstrated that "PC-Simulation" is a good and powerful tool in R&D. Details of Simulation are provided below according to the headings. The present invention provides a graphical user interface that includes a desktop workspace with a background.

1. Configuration

The "Simulation" package has been installed on a server. Here, MATLAB can be installed on client devices, where each of the client users accesses Simulation on the server. Once the MATLAB program has been installed on the client computer, the MATLAB icon is prompted on the computer. To launch the MATLAB program, the user double-clicks on the MATLAB icon.

2. Commands

Having launched the MATLAB program, a MATLAB command window with a few lines of notes is shown. There is a sign >> prompt on the left of the screen, followed by a cursor, which means that it is ready to receive a command. This command window is also called "workspace". It is used to enter commands, display results and error messages.

As an example, a few useful commands in MATLAB are set forth in Table III.

TABLE III

| Command | Description |
| --- | --- |
| whos | list all the variables in the memory |
| cd | change directory |
| ls | list all the files in the directory of "work" |
| dir | the same as ls |
| clc | erase all in the command window |
| clear | delete all the variables in the memory |
| clear variable name | only delete the variable with that name |
| path | list MATLAB path |
| savefilename variablename | save variable or variables into a .mat file with filename, and store in the "work" directory |
| save filename variablename | ascii save to a text file that can be loaded into excel |
| load filename | load variable or variables from the file into the workspace |
| global variablename | enable to list global variables in the workspace |
| delete filename | delete the file from the disk ("work" folder) |
| A = B; | assign matrix A equal to B |
| A = B'; | assign matrix A equal to B transpose |
| A = B(3:5,:); | A matrix consists of the rows 3 to 5 of B matrix |
| A = B(:,2:9); | A matrix consists of the columns 2 to 9 of B matrix |

The convention of data matrix set in chemometrics is that columns are variables (sensors) and rows are samples (exposures). For example, A(2,12) is referred to as data element on the second row (the second exposure) and the 12th column (sensor #12). A semicolon (;) at the end of command line will suppress the data display on the workspace.

Sometimes it is desirable to manipulate the data to delete rows (samples) or columns (variables) from a matrix. Here, command—delsamps is used. To delete row 12 from a matrix called data, type in
>>a =delsamps(data, 12);
where a is the result matrix that comes from data without row 12.

To delete column 10 from a matrix called data, type in
>>b=delsamps(data', 10)';
where b is the result matrix that comes from data without column 10.

3. Import and Export Data

Using save filename variablename-ascii command, the data file can be saved in the MATLAB workspace to a text file (tab-delimited). Then, it can be loaded into a spreadsheet such as Excel™ by Microsoft Corporation. On the other hand, if a data matrix exists in Excel, the data file can be saved to a tab-delimited text file. This can be done with data matrix without headers. From the file menu of the MATLAB workspace, check "load workspace", a dialogue box can then be launched. Next, any table-delimited data file can be loaded into the MATLAB workspace.

4. Method of Operation

The present method begins with a startup procedure. Here, upon the cursor (>>|) prompt on the MATLAB workspace, "simulhh" starts the PC-Simulation program. The PC-Simulation GUI 500 shown in FIG. 5A, appears on the terminal. The figure is merely an example, which should not limit the scope of the claims herein. One of ordinary skill in the art would recognize many other variations, modifications, and alternatives. The GUI includes at least the following parts:

(a) A series of pop-up menus 501 on the left panel simulate data loading, and data preprocessing.

(b) A graphical display 503 at the center of the GUI shows the images and plots of simulation.

(c) A mini command window 505 at the lower center of the GUI prompts the computation status and displays the results of simulation.

(d) A list-box and a push button (Load Training) 507 on the top right panel of GUI simulate the handheld type data loading. During operation, samples are loaded via one class after another class 509. The outlier, which is data outside an acceptable boundary, will be found and removed. The class information will be attached. Using "Save" and "load" buttons 507, training data can be saved to a file and can be reloaded into the workspace. A pop-up menu "Pattern Recognition" 511 on the right panel contains many algorithms for pattern recognition. They will be discussed in detail later.

(e) A push button "Auto CV" 513 initiates the auto cross validation mode. The program will alternatively make a subset of the training data and use its class information to build models, and use the models to predict the rest of the training data. After calculating all the combination of scaling and algorithms, the program will make a percentage list of correct predictions. The list will be shown on the mini command window. From there, a judgment can be made as to which algorithm works better in the application.

(f) An "info" button 517 displays the program information on the mini command window.

(g) A "Close" button 519 will stop and close the GUI program.

Figure 5A:
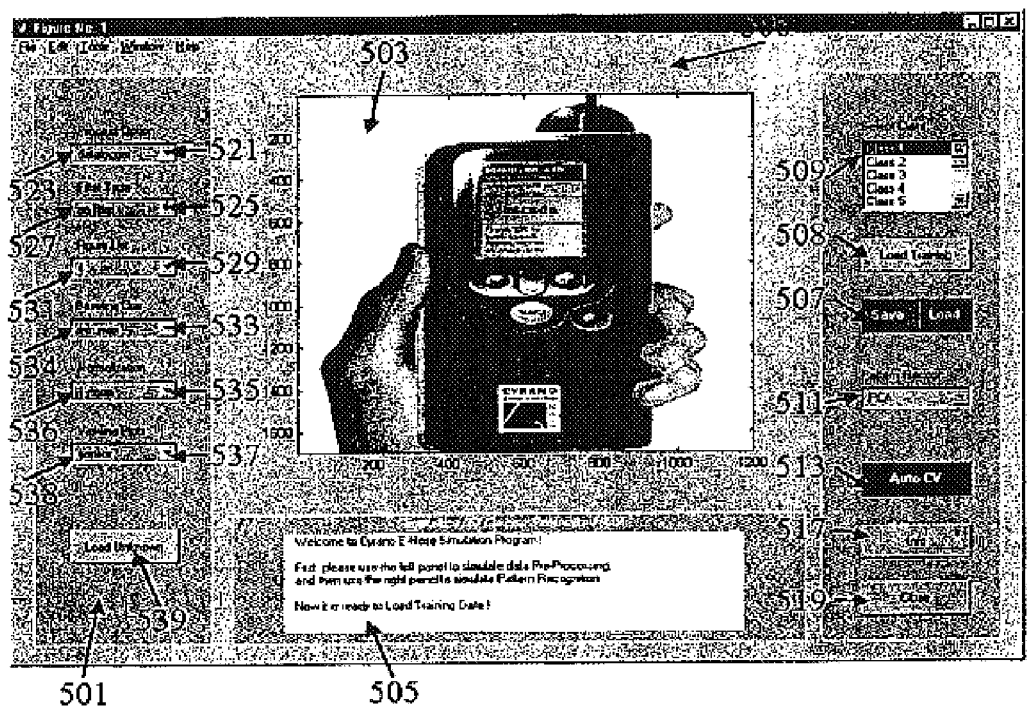
FIGS. 5A to 5L are simplified diagrams of an illustration of an example according to the present invention.

The GUI set forth in FIG. 5A is merely an example. It should only provide the reader an understanding of the present example, without unduly limiting the scope of the claims herein. One of ordinary skill in the art would recognize many other variations, modifications, and alternatives.

5. Load Data

After the data is loaded, the arrow 521 on the top-left pop-up menu of "Process Option" uncovers two choices, which pop-up, i.e., "Labnose" and "Datalogger" 523. A cursor can be moved with the mouse button down to highlight "Labnose" and then released if chemical lab data is loaded from a file collected from the Keithley Instrument, which gathers resistance data. Having done this, a dialogue box browser will appear. From there, the data file can be searched through the hard disk. Once a desired file is found, the open button retrieves the data from that data file. In a similar way, the "Datalogger" menu can be highlighted to load the data file collected from the Datalogger from the above capturing device. The mini command window will show the status of data loading. When the data loading is done, the method goes to the next processing step to choose one of the digital filters.

6. Digital Filtering

The data collected from some chemical sensors are sometimes accompanied with glitches and relative high frequency noise (compare to the signal frequency). Here, the signal to noise ratio (SNR) is often important for pattern recognition especially when concentrations of analytes are low, exceedingly high, or not within a predefined range of windows. In such cases, it is important to boost the signal to noise ratio using the present digital filtering technology. Multiple digital filters have been implemented in the Simulation, e.g., Zero Phase Filter, "zero phase", Adaptive Exponential Moving Average Filter, "exp-mov-avg", and Savitzky-Golay Filter, "savitzky-go". In operation, the mouse can be used to pull down an arrow 525, which displays the filters 527. The mouse is used to highlight one of the filters to select it. In some embodiments, the program will run that digital filter immediately after releasing the mouse. As merely an example, some details of such filters are set forth below.

(a) Zero-Phase Filter uses the information in the signal at points before and after the current point, in essence "looking into the future," to eliminate phase distortion. Zero-Phase Filter does use the z-transform of a real sequence and the z-transform of the time reversed sequence. Preferably, the sequence being filtered should have a length of at least three times the filter order and it tapers to zero on both edges.

(b) Savitzky-Golay Filter performs Savitzky-Golay smoothing using a simple polynomial to a running local region of the sample vector. At each increment, a polynomial of order is fitted to the number of points (window) surrounding the increment.

(c) Both Zero-Phase Filter and Savitzky-Golay Filter are post data process type filters. To the contrary, Adaptive Exponential Moving Average Filter can be used as a real-time filter. It does not need to store the whole scan of data into the memory and then process it. Currently the filter window is set at 11 points and it was found that Savitzky-Golay Filter gives a good result of data smoothing without significant distortion.

Although the above has been generally described in terms of specific filters, those of skill in the art will be aware of other filters suitable for use in the present invention.

7. Viewing Sensor Responses

Figure 5B:
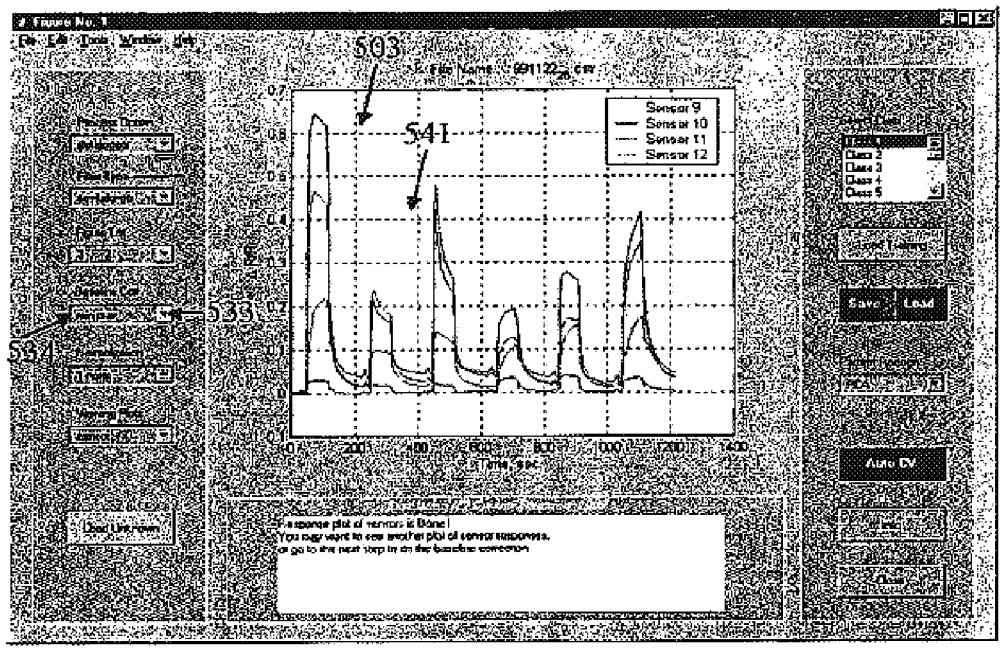

Sensor responses can be viewed using the present GUI 503, which illustrates ΔR/R against time in seconds. Another pop-up menu 531 on the left is called "Figure List". A click on the arrow 529 displays a list from 1 to 16. Each figure has the responses of four sensors in order. For example, FIG. 1 contains responses of sensor 1 to 4. Likewise, FIG. 2 contains responses of sensors 5 to 8. Move the mouse arrow to highlight the figure number 3, a response plot of sensors 9 to 12 with filtered and without filtered data will display on the graphical window as shown in a diagram of FIG. 5B, for example. Like reference numerals are used in this Figure as the previous Figure for easy referencing, without limiting the scope of the claims herein. As shown, the diagram illustrates a filter response 541 for each of the sensors (e.g., sensor 9, sensor 10, sensor 11, sensor 12) in the array. Here, the filtered data are usually in dark colors, such as red, blue, and black. If the data set is huge and has many exposures, the plot will be packed with response peaks and it could be hard to view the detail. By way of the present example, it is possible to view the detail of data preprocessing. The example also allows noise levels for each of the sensors. Additionally, the example illustrates how well the filter worked. The example also allows how the sensor responds to different analytes within the certain exposure time. The example also allows us to examine how the baselines drift (which is, for example, a nominal change in sensor resistance over time). In these examples, it may be desirable to load a piece of data, such as six exposures along the horizontal time axis or less as shown. Once the piece of data has been loaded, pre-processing can be performed. Using, for example, Wordpad by Microsoft Corporation, it is possible to cut and paste the data to create a subset of the data file. Once the desired filter has been found and used, the present method goes to a baseline correction step, as indicated below.

8. Baseline Correction

Figure 5C:
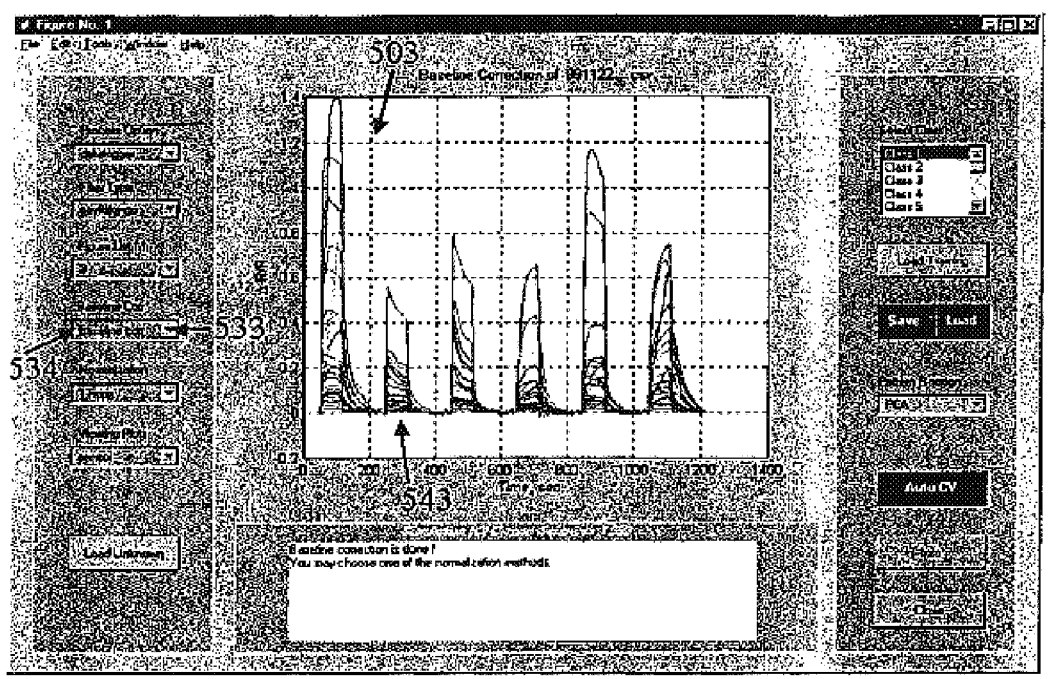

Depending upon the embodiment, there can be many different ways to implement a baseline correction method. In the present example, three methods for baseline correction have been implemented in the simulation. These correction methods were called "min max", "baseline corr", and "extrapolate". Selection occurred by clicking 533 the popup menu of "baseline corr", and selecting 534 one of the methods. The program guided by the flags set in the data file runs the baseline correction method according to user's choice, finds the response peaks, calculates the ΔR/R, and plots the ΔR/R vs. time stamps. It also calculates the maximum ΔR/R and the maximum slope of ΔR/R for further processing. As shown in FIG. 5C, the responses of all the sensors after baseline correction are displayed 503. In the graph, 32 traces of sensor responses with six exposures vs. time are plotted. As noted, the baseline drift 543 has been corrected as shown in FIG. 5C as compared to the responses in the previous Figures, which illustrate varying baseline displays. Weighting, such as Zero-Weighting on insignificant signals, is also included in the program. The threshold has been set at SNR equal to three. Once baseline drift has been corrected, the present method undergoes a normalization process, although other processes can also be used.

9. Normalization

Normalization is provided in the following manner. Here, the user clicks on the popup menu of Normalization and three choices: "none", "1-norm", and "2-norm" appear, as illustrated in part in FIG. 5D. Depending upon the embodiment, other choices may also appear. The convention of the data matrix after the baseline correction is to set samples (exposures) along the rows and variables (sensors) along the columns. The normalization is a row wise operation. 1-norm is the so-called area normalization. After 1-norm, the sum of data along each row is unity. 2-norm is the so-called vector length normalization. After 2-norm, the sum of data squared of each row equals unity. From studies, it is concluded that the ΔR/R of the sensor is proportional to the concentration if the sensor reaches equilibrium during the exposure time. Theoretically the normalization of such data should make a same response pattern even if the sensor is exposed to a different sample concentration.

Figure 5D:
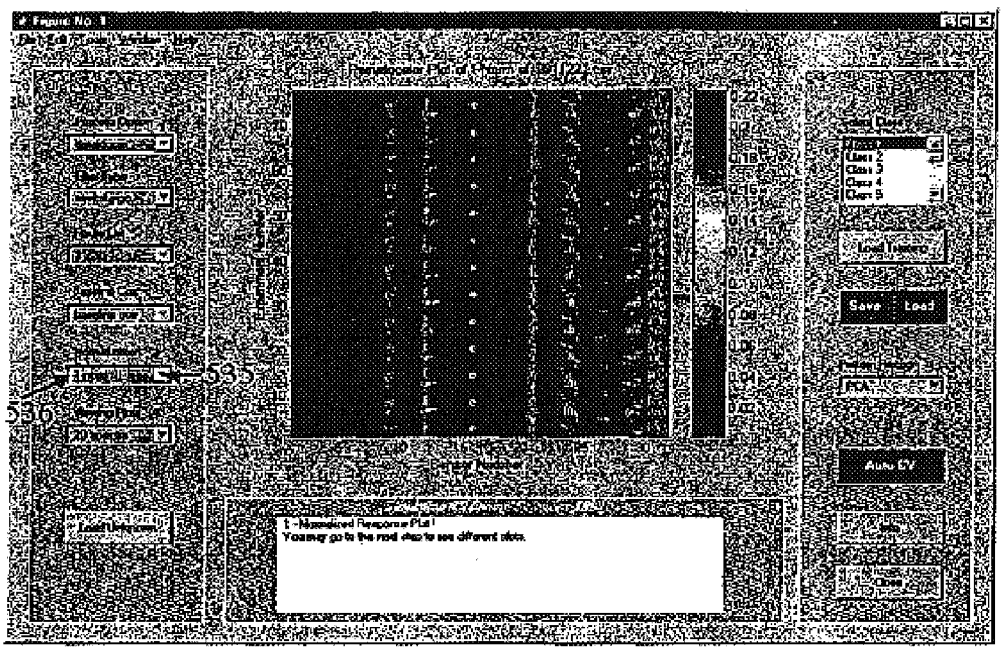

Here, a pseudo-color graph of 1-norm data is shown in the simplified diagram of FIG. 5D with a color bar. The graph is plotted as sensor number vs. sample number. The peaks are marked red and the valleys are in dark blue. The pattern in the graph is repeated as samples are counted from 1 to 6. Up to this step, the training data set has been created. Click on the workspace window to bring it to the front and type "whos," and the data set called trainpk with variable and size info display on the workspace will be displayed.

10. Viewing Plots

Figure 5E:
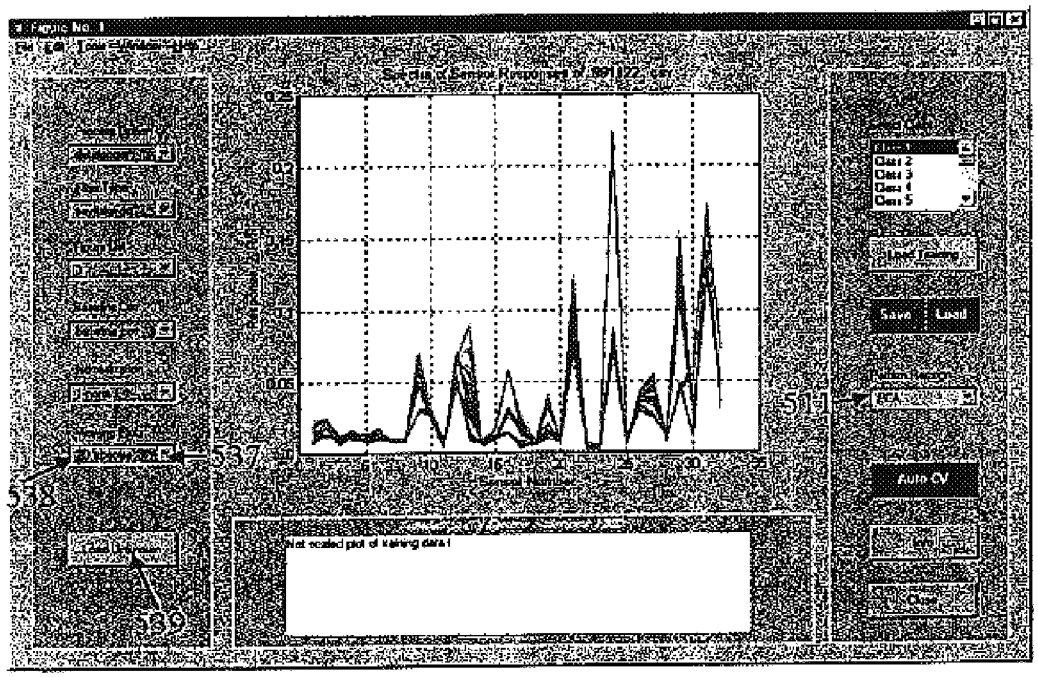

The present method also allows for viewing the plots in a variety of different configurations, as illustrated in FIG. 5E. The popup menu of Viewing Plots will not alter the data of "trainpk", but will allow to view different plots such as 2D spectra, 3D plots of sensors, mean-centered, and auto-scaled. One of the useful plots is the 2D spectra plot that is shown in the FIG. 5E. Keeping these plots in the file folder, any sensor can be followed for drifting and check consistency of sensor responses day after day.

11. Save Preprocessed Data

To save the preprocessed data, trainpk, the trainpk can be assigned to a variable with a new name first and then save it to a mat file or ascii file. If a file name called ttb1122 is to be saved, the command window can be entered as follows,

```
>>ttb1122=trainpk;
>>save ttb1122 ttb1122;
```

A ttb1122.mat file is saved in the "work" folder, or

```
>>save ttb1122 ttb1122-ascii;
```

A ttb1122.txt file is saved in the "work" folder.

12. Auto Preprocessing

After having gone through all the preprocessing steps, the preprocessing choices have been selected. The GUI shows the choices on their popup windows and keeps them intact. In certain aspects, it is desirable to preprocess many data sets, here the auto mode can be run by pressing the button of "Load Unknown" at the bottom left of the GUI. The program follows the previously set preprocessing steps and runs automatically, but can also be run semi-automatically. The resulting matrix is called samplepk. To save samplepk, the samplepk can be assigned to a variable with a new name first and then save it to a mat file or ascii file as trainpk, for example:

```
>>ttb1123=samplepk;
>>save ttb1123 ttb1123.
```

On the top-right panel, there is a list box, "Select Class" and a few push buttons, "Load Training", "Save", and "Load". If each data file is in one class, these buttons can be used to run auto preprocessing. Here is the procedure:

(a) Use the mouse button to highlight class info in the list box on the top-right panel, e.g., Class 1 or Class 2 or . . .

(b) Push "Load Training" button. The GUI will automatically run through the preprocessing steps and use PCA to screen and delete the outliner if there is any. If the number of samples in that class is less than ten, the program will ask for more loading of samples belonging to that class. In that case, it is desirable to push "Load Training" button again.

(c) Use the mouse button to highlight another class info in the list box.

(d) Push "Load Training" button to load samples belonging to that class.

(e) Repeat the same procedure until all the samples have been loaded.

(f) The result is that the training set matrix, trainpk, and class vector, class, have been created in the workspace.

(g) Pushing "Save" button, will save trainpk and class into a mat file with a different file name.

(h) Later on, if the "Load" button is pushed the file can be reloaded into the workspace.

13. Comments on Data Preprocessing

To perform pattern recognition, the choices of preprocessing for all the data sets must often be consistent; otherwise the prediction will generally not work in an efficient manner. To build model from a training set, the matrix is assigned the name of trainpk, for example. Here, the number of samples in each class is maintained the same. A class info vector called class is created unless the right panel is used for data preprocessing. For the turn-table data with six classes, assign class =[1 2 3 4 5 6 1 2 3 4 5 6 . . . ]. For the labnose data, assign class=[1 1 1 1 1 1 1 1 1 1 2 2 2 2 2 2 2 2 2 3 3 3 3 . . . ]. In certain instances, it is desirable to make trainpk from data set ttb1122 and to tailor it, thus, type:
>>trainpk ttb1122(13:72,:).

Then trainpk will have 60 rows from row 13 to 72 of the matrix ttb1122. To do prediction, assign the unknown data set (matrix) to the name of samplepk. Thereafter, type >>samplepk=ttb1123(13:18,:). Then samplepk will consist of six rows of the matrix ttb1123.

The data preparation has been described in this section. As long as trainpk and the class vector are compatible, the program is then ready to run the pattern recognition programs.

14. Pattern Recognition

The popup menu "Pattern Recogn" 511 at the middle of right panel initiates the pattern recognition algorithms. Click on the arrow 511 to see a pull-down menu with all the abbreviations as described in Table I above. As discussed above, the top two menus, PCA and HCA, are unsupervised learning methods. They are used for investigating training data. The other four algorithms, KNN CV, SIMCA CV, Canon CV, and Fisher CV, are supervised learning methods used when the goal is to construct models to be used to classify future samples. These algorithms will do cross validation, find the optimum number of parameters, and build models 15. Principal Components Analysis (PCA)

Principal Component Analysis (PCA) is an unsupervised method that reduces the number of required variables to analyze similarities and differences amongst a set of data. The method produces a scores plot for this analysis. The number of principal components (PC's) is automatically determined. Each axis of the graph is assigned a PC number, and the percent variance captured with the particular PC is shown along the axis.

Figure 5F:
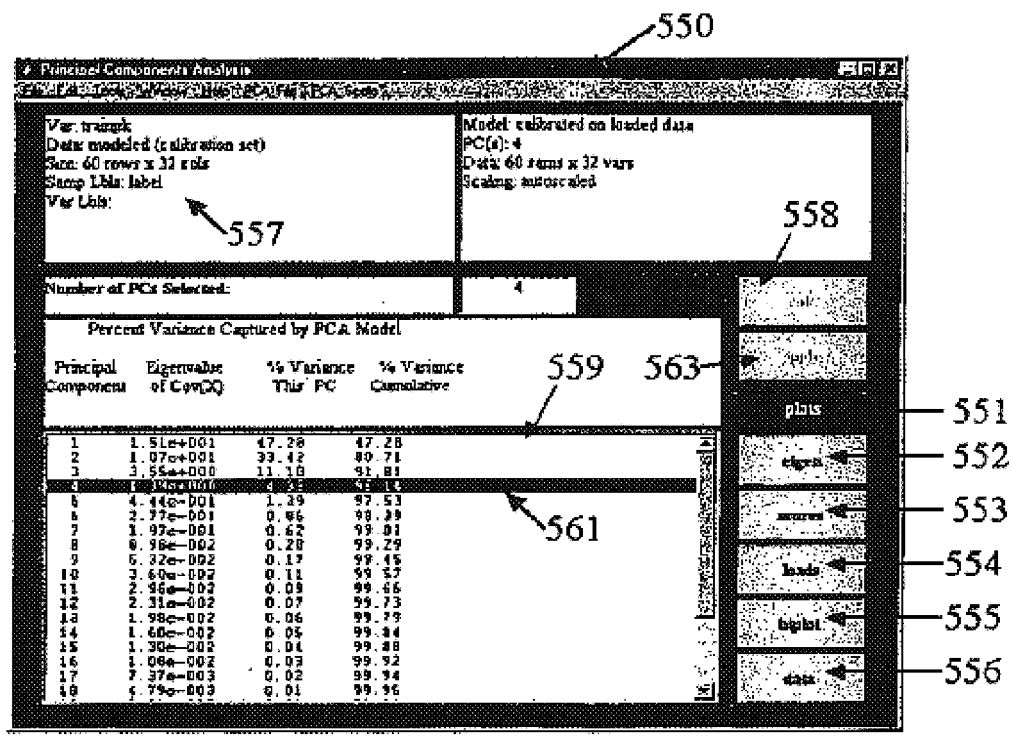

PCA of data may be performed utilizing a number of software programs. One such program is the PLS_Toolbox available from Eigenvector Research, Inc. of Manson, Wash. To perform PCA using this tool, "PCA" is highlighted in the popup menu of "Pattern Recogn" opens a PCA GUI. From the top menu bar of that GUI, click on PCA_File, and highlight Load Data. The file trainpk can be selected to load into the PCA program. When it is done, the window looks similar to output 550 in FIG. 5F. On the top-left corner 557, it shows that trainpk has been loaded with size 60 rows×32 columns. The push button calc 558 has been clicked and the program will run PCA, calculates Eigen values and Eigen vectors, and lists all the percent variance captured by PCA model as shown. From the table 559, it is desirable to find that four principal components already have captured 96.05% of variance. Using more PCs may not improve the PCA model much but capture more noise. For example, in certain instances, it desirable to choose four PCs. Thus, click on the line of 4 PCs 561. That line of data will be highlighted, as shown. Next, click on the button apply 563, and the model with four PCs is calculated. Five plot push buttons 551, eigen 552, scores 553, loads 554, biplot 555, data 556 are highlighted.

Figure 5G:
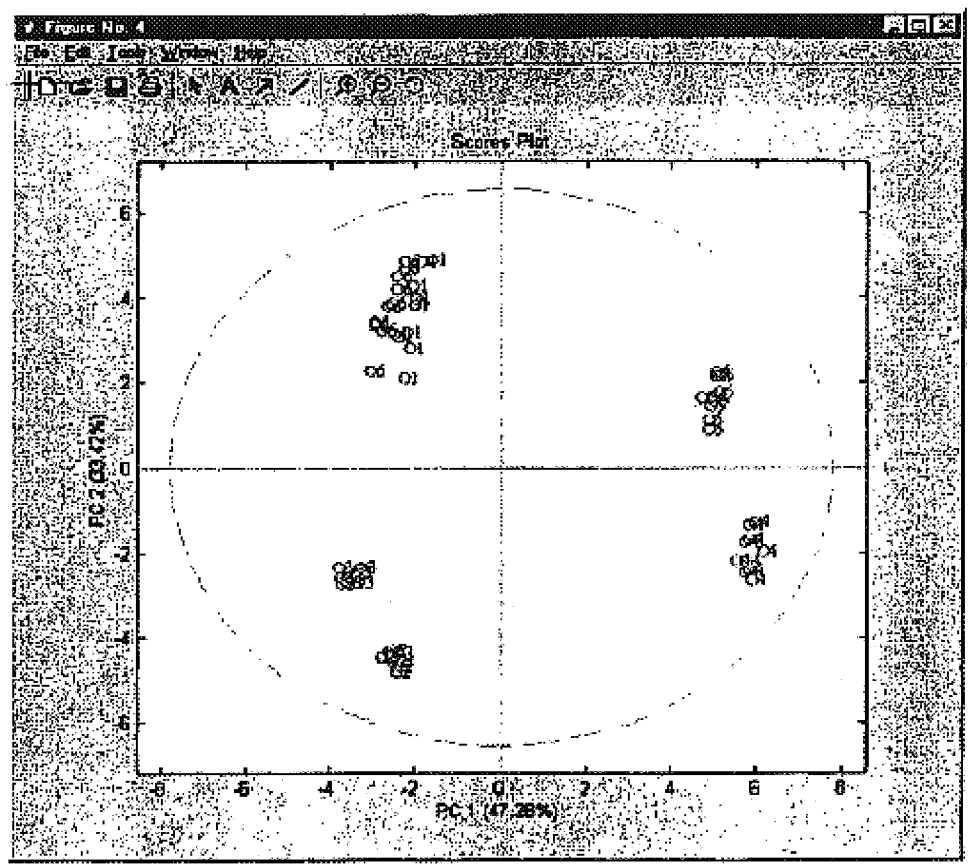

In other aspects, push the button "scores," and choose to plot PC1 vs. PC2, and see a Scores Plot as displayed in a spatial configuration of FIG. 5G. Here, the Fig. depicts that the training data has six classes, and are grouped well except class 1 and class 6 with a little overlap. In some embodiments, make a 3D plot by choosing three PCs to plot. To print a hard copy, the "spawn" button is selected to create a separate plot window, which can be printed.

Figure 5H:
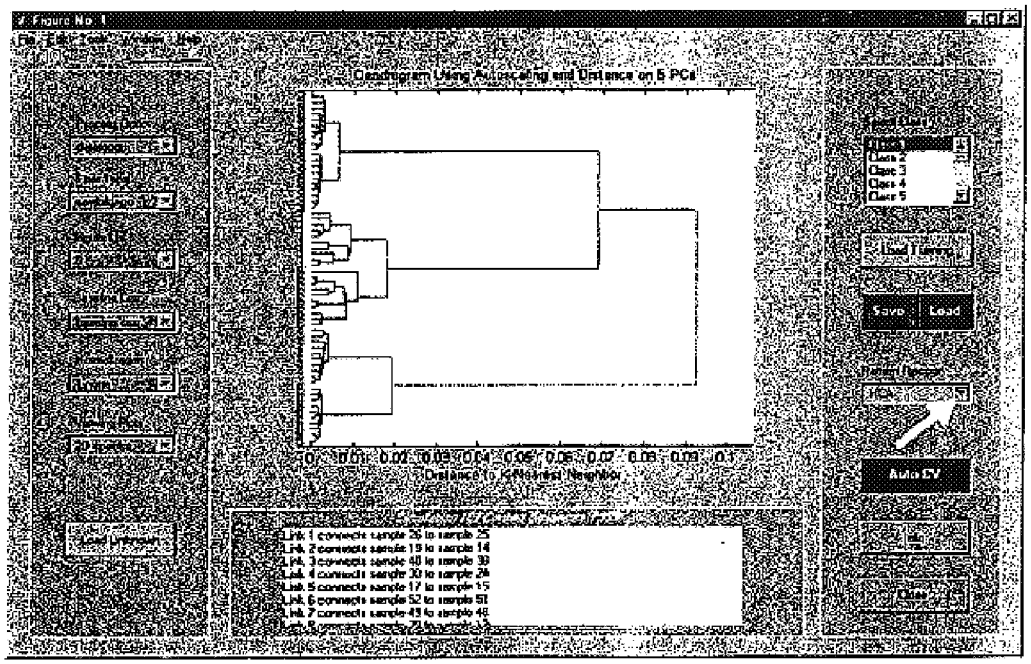
Figure 5I:
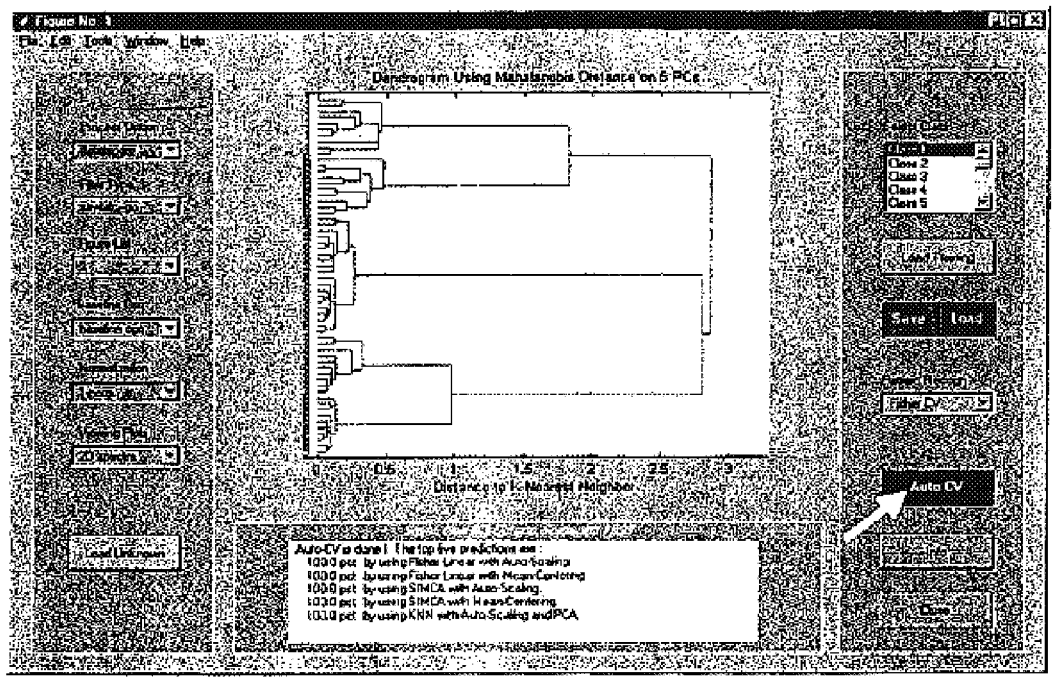
Figure 5J:
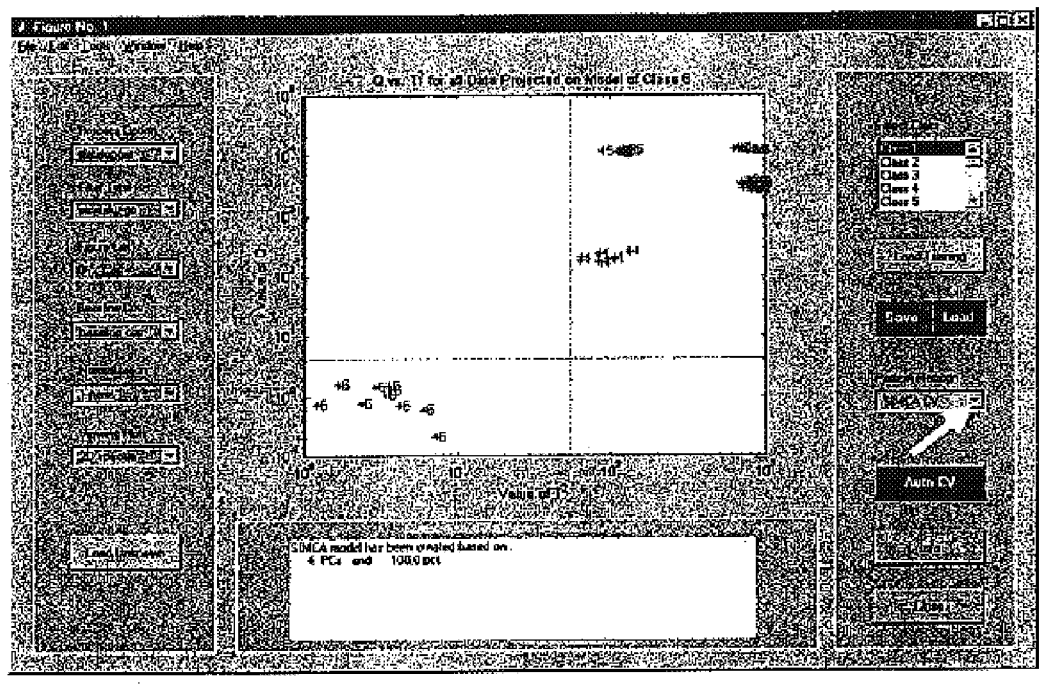
Figure 5K:
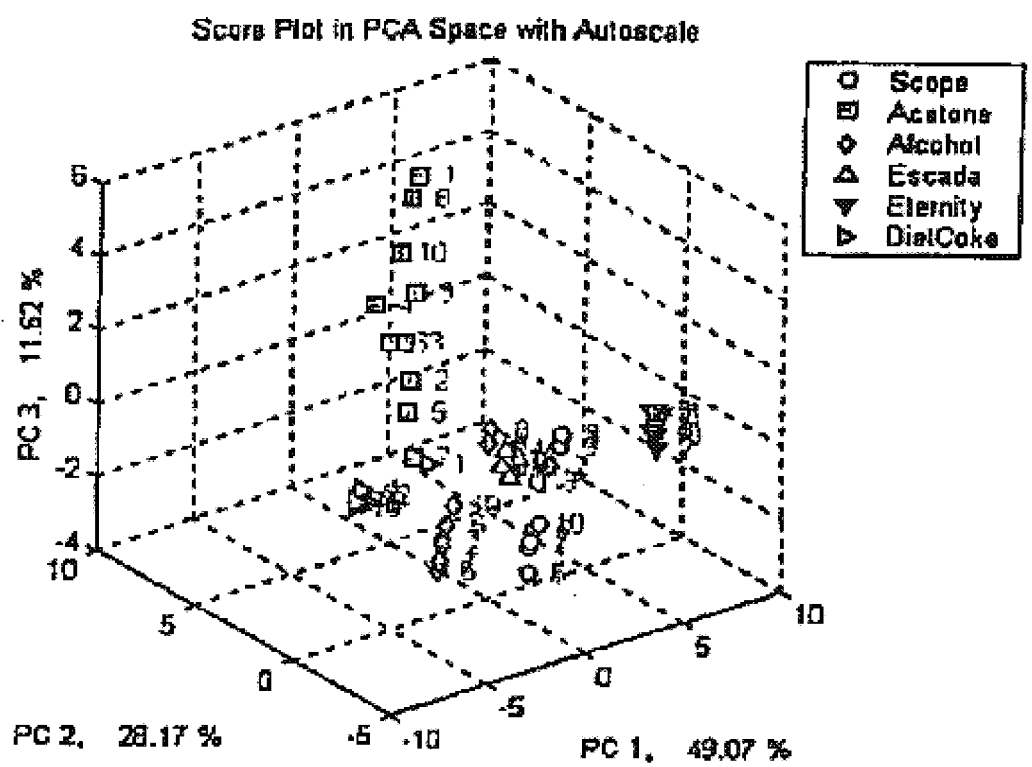
Figure 5L:
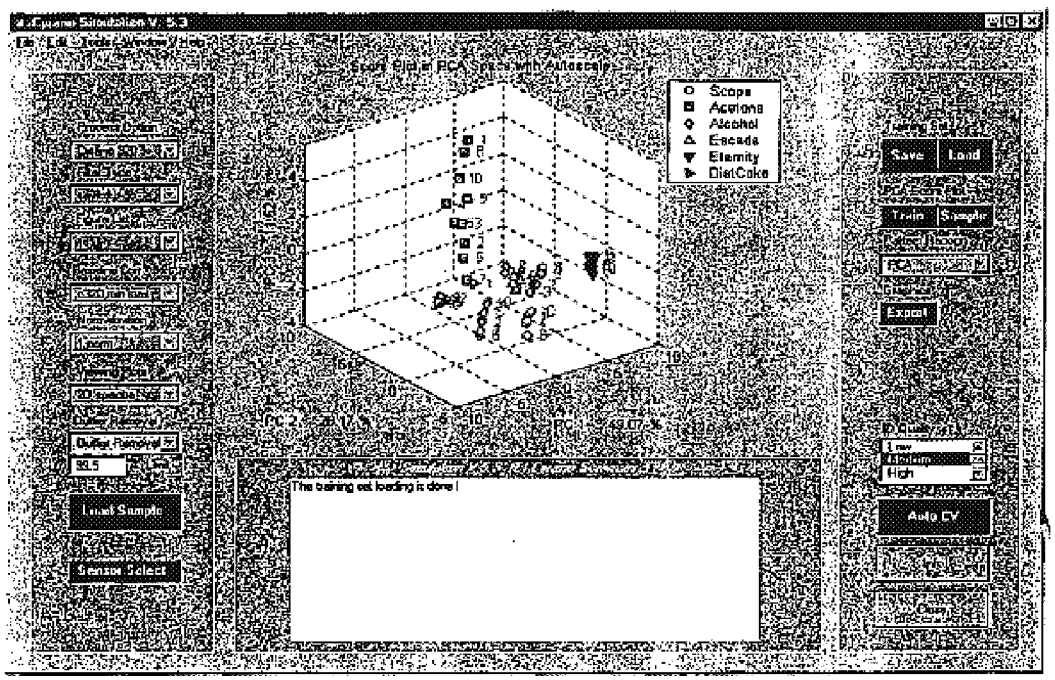

FIGS. 5K and 5L show alternative approaches for performing PCA. FIG. 5K shows a three-dimensional Scores Plot 590. FIG. 5L shows a graphic user interface for this approach, wherein clicking the arrow of "Pattern Recogn" and highlighting "PCA" causes a pop-up window to appear. This pop-up window allows the user to select the method of pre-processing (i.e. no pre-processing, mean-center, or autoscale). As shown in FIG. 5L, the Scores Plot then appears. In the menu option, the user may select "zoom in", "zoom out", or "rotate" to change the view of the scores plot in the graphical display.

16. Mean Centering and Autoscaling

The default setting in the PCA GUI is autoscaling. From the menu bar of the PLS_Toolbox application, by selecting PCA_Scale, the method can change among no scaling, mean center, and autoscaling. PCA is scale dependent, and numerically larger variables appear more important in PCA. In certain instances, the data that varies around the mean is of interest. Mean centering is done by subtracting the mean off the variables in each column, thus forming a matrix where each column has a mean of zero. Autoscaling is done by dividing each variable (already mean centered) in each column by its standard deviation. The variables of each column of the resulting matrix have unit variance. The button, auto CV, will run the algorithms with mean centering and autoscaling to do cross validation and find out what combination gives the best prediction.

17. Hierarchical Cluster Analysis (HCA)

Hierarchical cluster analysis (HCA) is an unsupervised technique that examines the inter-point distances between all of the samples, and presents that information in the form of a two-dimensional plot called a dendrogram as shown in FIG. 5H. To generate the dendrogram, HCA forms clusters of samples based on their nearness in row space. Click the arrow of "Pattern Recogn" and highlight "HCA", the GUI enables different approaches to measure distances between clusters, e.g., mean centering vs. autoscaling; single vs. centroid linking; run PCA vs. not run PCA; Euclidean vs. Mahalanobis distance.

After having run the HCA, the mini window and the workspace lists all the links from the shortest distance to the longest distance. The clustering information is also shown in the dendrogram. The ordinate presents sample numbers and their class info; while the abscissas gives distances between sample points and between clusters. The six classes are well observed in that graph. The distances between sample points and between clusters can be found from the abscissas.

18. Auto Cross Validation

The method also performs a cross validation technique. Here, click the button, "Auto CV," and the Simulation GUI will run cross validation using all the supervised techniques with the combination of either mean centering or autoscaling. The Auto CV finds the optimum combination of scaling and algorithm, the optimum number of principal components, and the optimum K in KNN CV. The results of top five predictions from Auto CV are presented in the mini window as shown in FIG. 5I. It may be desirable to use the information to construct other models to get better classification.

In the Simulation program, an auto cross-validation algorithm has been implemented. Cross-Validation is an operation process used to validate models built with chemometrics algorithms based on training data set. During the process, the training data set is divided into calibration and validation subsets. A model is built with the calibration subset and is used to predict the validation subset. One approach of dividing the training data set into calibration and validation subsets is called "leave-one-out", i.e., take one sample out from each class to build a validation subset and use the rest samples to build a calibration subset. This process is repeated using different subsets until every sample in the training set has been included in one validation subset. The predicted results are stored in an array. Then, the correct prediction percentages (CPP) are calculated, and are used to validate the performance of the model.

In the Simulation program, the cross-validation with one training data set can be applied to all the models built with different algorithms, such as K-Nearest Neighbor (KNN), SIMCA, Canonical Discriminant Analysis, and Fisher Linear Discriminant Analysis, respectively. The results of correct prediction percentages (CPP) show the performance differences with the same training data set but with different algorithms.

During the model building, there are several parameters and options to choose. To build the best model with one algorithm, cross-validation is also used to find the optimum parameters and options. For example, in the process of building a KNN model, cross-validation is used to validate the models built with different number of K, different scaling options, e.g., mean-centering or auto-scaling, and other options, e.g., with PCA or without PCA, to find out the optimum combination of K and other options.

Auto-Cross-Validation has been implemented in the Simulation GUI via one push-button. It will automatically run the processes mentioned above over all the algorithms with the training data set to find out the optimum combination of parameters, scaling options and algorithms. Using that information, it is possible to build a model to get better classification capability.

19. Construct Models

In some embodiments, the method constructs models. Here, click the popup menu, "SIMCA CV," and the Simulation GUI will construct a SIMCA model based on choice of scaling. After it is done, the graph window shows the plots of Q vs. $T^2$ of each class, and the mini window displays that 4 PCs have been chosen to construct the model and the predictions of cross validation are, say, 100% correct. A data structure (the model) named simcamod has been created in the workspace if whos is typed in the workspace. A KNN Model, knnmod, Canonical Model, canmod, and Fisher Linear Discriminant Model, fldmod, can be constructed in the same way by clicking and highlighting the popup menus, respectively. Validation can occur by typing whos to validate how many models are there in the workspace, as illustrated by FIG. 5J.

20. Make Predictions

The unknown samples to be predicted are named as samplepk. In certain aspects, there are two ways to make unknown samples, samplepk:

Push "Load Unknown" button, the Simulation GUI will load unknown samples from a raw data file, preprocess it automatically and create samplepk.

Tailor the preprocessed data as mentioned before and assign it to samplepk, such as >>samplepk =ttb1123 (13:18,:).

To make a prediction, click the popup menu and highlight corresponding menu to initiate prediction run. KNN Prd will run KNN model on the unknown samples, and present the prediction results in the mini command window. The prediction results will be like:

Unknown 1 belongs to class 1; Goodness Value=−0.8976

Unknown 2 is close to class 2; Goodness Value=4.8990

If the Goodness value is less than 4, it will be considered belonging to that class.

Click on the buttons of SIMCA Prd, Canon Prd, and FisherPrd respectively, and the Simulation GUI will do the same. The prediction results with the information of probabilities or confidence levels will be presented in the mini command window.

SIMCA Prd gives prediction with rms normalized distance levels. If the level is greater than 1.414, the unknown is not considered belonging to that class, but it is close to that class.

Canon Prd provides predictions with probability level values. If the probability level is less than 0.99, the unknown sample is considered belonging to that class; otherwise, it will be pointed as belonging to the closest class.

While the invention has been described with reference to certain illustrated embodiments this description is not intended to be construed in a limiting sense. For example, the computer platform used to implement the above embodiments include 586 class based computers, Power PC based computers, Digital ALPHA based computers, SunMicrosystems SPARC computers, etc.; computer operating systems may include WINDOW NT, MacOs, UNIX, VMS, etc.; programming languages may include C, C++, Pascal, an object-oriented language, HTML, XML, and the like. Various modifications of the illustrated embodiments as well as other embodiments of the invention will become apparent to those persons skilled in the art upon reference to this description.

In addition, a number of the above process can be separated or combined into hardware, software, or both and the various embodiments described should not be limiting. As will be appreciated by one of skill in the art, the present invention can be embodied as a method, data processing system, or computer program product. Accordingly, the present invention can take the form of an entirety hardware embodiment, an entirely software embodiment or an embodiment combining software and hardware aspects. Furthermore, the present invention can take the form of a computer program product on a computer-usable storage medium having computer-usable program code embodied in the medium. Any suitable computer readable medium can be utilized including hard disks, CD-ROMs, optical storage devices, or magnetic storage devices. It will be understood, therefore that the invention is defined not by the above description, but by the appended claims. All publications, patents, and patent applications cited herein are hereby incorporated by reference for all purpose in their entirety.

What is claimed is:

1. A system comprising memory including a computer code product for training computing devices for classification or identification purposes for one or more substances capable of producing olfactory information, the memory comprising:
   a code directed to providing at least a first data related to one or more substances from a first node and a second data related to one or more substances from a second node to a computing device, the data being comprised of a plurality of characteristics to identify the substance, wherein the first node or the second node is connected over a computer network;
   a code directed to normalizing at least one of the characteristics for each of the first data and the second data;
   a code directed to correcting at least one of the characteristics for each of the first data and the second data;
   a code directed to processing one or more of the plurality of characteristics for each of the first data and the second data in the computing device using pattern recognition to form descriptors to identify the one or more substances; and
   a code directed to storing the set of descriptors into a memory device coupled to the computing device, the set of descriptions being for analysis purposes of the one or more substances and performing a combined analysis based on the first data and the second data.

2. The system of claim 1 wherein the characteristics can be selected from olfactory information, temperature, color, and humidity.

3. The system of claim 1 wherein the pattern recognition is a Fisher Linear Discriminant Analysis.

4. The system of claim 1 wherein the first data and the second can be selected from a transient stream of data or from a static source of data.

5. The system of claim 1 wherein the steps are performed continuously in the computing device.

6. The system of claim 1 wherein the data are captured from an array of olfactory sensors.

7. The system of claim 6 wherein the olfactory sensors are comprised of a polymer component.

8. The system of claim 1 wherein the first data and the second data are provided through a worldwide network of computers, the worldwide network of computers comprising the Internet.

9. The system of claim 1 wherein the first data and the second data are captured from a first sensor and a second sensor, respectively, disposed in an array.

10. The system of claim 1 wherein the first data and the second data are captured from a first sensor and a second sensor, respectively, disposed in an array and transported through the Internet.

11. A system including memory and computer codes for preprocessing information for identification or classification purposes, the system comprising:
    a code directed to acquiring a voltage reading from a sensor of a sensing device, the sensor being one of a plurality of sensors that are disposed in an array;
    a code directed to determining if the voltage is outside a baseline voltage of a predetermined range; and
    a code directed to rejecting the sensor of the sensing device for use in acquiring sensory information, if the voltage is outside the predetermined range.

12. The system of claim 11 further comprising a code directed to repeating steps of acquiring and determining for any other sensors in the plurality of sensors in the array to detect a faulty sensor that is outside the predetermined range.

13. The system of claim 11 wherein each of the sensors in the array acquires a respective voltage reading simultaneously.

14. The system of claim 11 further comprising a code directed to exposing at least one of the sensors to a sample and acquiring a sample voltage from the sample.

15. The system of claim 11 further comprising a code directed to exposing at least one of the sensors to a sample and acquiring a sample voltage from the sample, if the sample voltage is outside a predetermined sample voltage range, reject the one exposed sensor.

16. The system of claim 11 wherein the plurality of sensors comprise an olfactory sensor, the olfactory sensor being comprised of a polymer component.

17. A system for classifying or identifying one or more substances capable of producing olfactory information, the method comprising:
    a process manager;
    an input module coupled to the process manager for providing at least a first data related to one or more substances from a first node and a second data related to one or more substances from a second node to a computing device, the data being comprised of a plurality of characteristics to identify the one or more substances, wherein one or both of the first node and the second node is connected to the input module over a computer network;
    a normalizing module coupled to the process manager for normalizing at least one of the characteristics for each of the first data and the second data;
    a patterning recognition module coupled to the process manager for processing one or more of the plurality of characteristics for each of the first data and the second data in the computing device using pattern recognition to form descriptors to identify the one or more substances; and
    an output module coupled to the main process manager for storing the set of descriptors into a memory device coupled to the computing device, the set of descriptions being for analysis purposes of the one or more substances and performing a combined analysis based on the first data and the second data.

18. The system of claim 17 wherein the characteristics can be selected from olfactory information, temperature, color, and humidity.

19. The system of claim 17 wherein the pattern recognition is a Fisher Linear Discriminant Analysis.

20. The system of claim 17 wherein the first data and the second can be selected from a transient stream of data or from a static source of data.

21. The system of claim 17 wherein the steps are performed continuously in the computing device.

22. The system of claim 17 wherein the data are captured from an array of olfactory sensors.

23. The system of claim 22 wherein the olfactory sensors are comprised of a polymer component.

24. The system of claim 17 wherein the system is provided in a computer.

25. The system of claim 17 wherein the pattern recognition module comprises a plurality of pattern recognition algorithms.

26. The system of claim 17 further comprising a data storage device coupled to the main process manager.

27. The system of claim 17 further comprising a network module coupled to the main process manager, the network module being coupled to a worldwide network of computers.

28. The system of claim 17 further comprising a network module coupled to the main process manager, the network module being coupled to a world wide network of computers, the input module being coupled to a sensor device comprising a plurality of sensors through the world wide network of computers.

29. A method for training computing devices for classification or identification purposes for one or more substances capable of producing olfactory information, the method comprising:

providing at least a first data related to one or more substances from a first node and a second data related to one or more substances from a second node to a computing device, the data being comprised of a plurality of characteristics to identify the one or more substances wherein the first node or the second node is connected over a computer network;

normalizing at least one of the characteristics for each of the first data and the second data;

correcting at least one of the characteristics for each of the first data and the second data;

processing one or more of the plurality of characteristics for each of the first data and the second data in the computing device using pattern recognition to form descriptors to identify the one or more substances; and storing the set of descriptors into a memory device coupled to the computing device, the set of descriptions being for analysis purposes of the one or more of substances and for a combined analysis based on the first data and the second data.

30. The method of claim 29 wherein the characteristics can be selected from olfactory information, temperature, color, and humidity.

31. The method of claim 29 wherein the pattern recognition is a Fisher Linear Discriminant Analysis.

32. The method of claim 29 wherein the first data and the second can be selected from a transient stream of data or from a static source of data.

33. The method of claim 29 wherein the steps are performed continuously in the computing device.

34. The method of claim 29 wherein the data are captured from an array of olfactory sensors.

35. The method of claim 34 wherein the olfactory sensors are comprised of a polymer component.

36. The method of claim 29 wherein the first data and the second data are provided through a worldwide network of computers, the worldwide network of computers comprising the Internet.

37. The method of claim 29 wherein the first data and the second data are captured from a first sensor and a second sensor, respectively, disposed in an array.

38. The method of claim 29 wherein the first data and the second data are captured from a first sensor and a second sensor, respectively, disposed in an array and transported through the Internet.

39. A method for teaching a system used for analyzing multidimensional information for one or more substances, the method comprising:

providing a plurality of different substances from at least two nodes connected over a computer network, each of the different substances being defined by a plurality of characteristics to identify any one of the substances from the other substances, the plurality of characteristics being provided in electronic form;

providing a plurality of processing methods, each of the processing methods being capable of processing each of the plurality of characteristics to provide an electronic fingerprint for each of the substances;

processing each of the plurality of characteristics for each of the substances through a first processing method from the plurality of processing methods to determine a relationship between each of the substances through the plurality of characteristics of each of the substances from the first processing method; processing each of the plurality of characteristics for each of the substances through a second processing method to determine a relationship between each of the substances through the plurality of characteristics for each of the substances from the second processing method; and processing each of the plurality of characteristics for each of the substances through an nth processing method to determine a relationship between each of the substances through the plurality of characteristics from each of the substances from the nth processing method;

comparing the relationship from the first processing method to the relationship from the second processing method to the relationship from the nth processing method to find the processing method that yields the largest signal to noise ratio to identify each of the substances; and selecting the processing method that yielded the largest signal to noise ratio, whereupon the relationships from the selected processing method provide an improved ability to distinguish between each of the substances using the selected processing method.

40. The method of claim 39 wherein the plurality of processing methods can comprise a method selected from PCA, HCA, KNN CV KNN Prd, SIMCA CV, SIMCA Prd, Canon Prd, and Fisher CV.

41. The method of claim 39 wherein the characteristics can be selected from olfactory information, temperature, color, and humidity.

42. A method for preprocessing information for identification or classification purposes, the method comprising:

acquiring a voltage reading from a sensor of a sensing device, the sensor being one of a plurality of sensors that are disposed in an array;

determining if the voltage is outside of a baseline voltages of a predetermined range; and if the voltage is outside of the predetermined range, rejecting the sensor of the sensing device for use in acquiring sensory information.

43. The method of claim 42 further comprising repeating steps of acquiring and determining for any other sensors in the plurality of sensors in the array to detect for a faulty sensor that is outside the predetermined range.

44. The method of claim 42 where each of the sensors in the array acquires a respective voltage reading simultaneously.

45. The method of claim 42 further comprising exposing at least one of the sensors to a sample and acquiring a sample voltage from the sample.

46. The method of claim 42 further comprising exposing at least one of the sensors to a sample and acquiring a sample voltage from the sample, if the sample voltage is outside of a predetermined sample voltage range, reject the one exposed sensor.

47. The method of claim 42 wherein the plurality of sensors comprise an olfactory sensor, the olfactory sensor being comprised of a polymer component.

48. A system for identifying one or more substances capable of producing olfactory information, the system comprising:
- a user interface apparatus comprising a display, a graphical user interface, and a central processor that receives data related to the one or more substances from at least two nodes connected over a computer network; and
- a process manager operably coupled to the display through the central processor, wherein the graphical user interface is capable of imputing an information object from a client to manipulate olfaction data and displaying the identity of the one or more substances and performing a combined analysis based on the received data from the at least two nodes.

49. The system of claim 48, wherein the information object is selected from the group consisting of digital filtering, preprocessing, pattern recognition, mean centering, autoscaling and cross validation.

50. The system of claim 49, wherein pattern recognition is selected from the group consisting of PCA, HCA, KNN CV KNN Prd, SIMCA CV, SIMCA Prd, Canon Prd, and Fisher CV.

51. The method of claim 29 wherein the data from the first node and the second node is data obtained for shipping container monitoring.

52. The method of claim 29 wherein the data from the first node and the second node is data obtained for perimeter monitoring.

53. The method of claim 29 wherein the data from the first node and the second node is data obtained for explosive monitoring.

54. The method of claim 29 wherein the data from the first node and the second node is data obtained for hazardous spill monitoring.

55. The method of claim 29 wherein the data from the first node and the second node is data obtained for radiation monitoring.

56. The system of claim 17, further comprising a database that comprises additional data for the combined analysis based on the first data and the second data.

* * * * *